(12) United States Patent
On

(10) Patent No.: US 9,498,153 B2
(45) Date of Patent: Nov. 22, 2016

(54) ENDOSCOPE APPARATUS AND SHAKE CORRECTION PROCESSING METHOD

(75) Inventor: Seigo On, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 807 days.

(21) Appl. No.: 13/440,800

(22) Filed: Apr. 5, 2012

(65) Prior Publication Data

US 2012/0262559 A1 Oct. 18, 2012

(30) Foreign Application Priority Data

Apr. 7, 2011 (JP) .................................. 2011-085435

(51) Int. Cl.
*H04N 5/232* (2006.01)
*A61B 5/11* (2006.01)
*H04N 5/225* (2006.01)
*A61B 5/00* (2006.01)

(52) U.S. Cl.
CPC ......... *A61B 5/1128* (2013.01); *H04N 5/23267* (2013.01); *A61B 5/1107* (2013.01); *A61B 5/6847* (2013.01); *H04N 2005/2255* (2013.01)

(58) Field of Classification Search
CPC .................. H04N 5/23267; H04N 2005/2255; H04N 5/23248; H04N 5/23251; H04N 5/23254; H04N 5/23264; A61B 5/6847; A61B 5/1107; A61B 5/1128
USPC .............................................. 348/65; 606/109
See application file for complete search history.

(56) References Cited

U.S. PATENT DOCUMENTS

| 4,322,740 | A | * | 3/1982 | Takemoto | .............. H04N 9/045 348/264 |
| 5,270,810 | A | * | 12/1993 | Nishimura | ............. H04N 5/335 348/220.1 |
| 6,417,887 | B1 | * | 7/2002 | Yamaji | .................... H04N 7/012 348/447 |
| 6,630,950 | B1 | * | 10/2003 | Ohkawara | .......... H04N 5/23248 348/208.11 |
| 8,315,448 | B2 | | 11/2012 | Takei | |
| 8,465,415 | B2 | | 6/2013 | Ogawa | |
| 2002/0131652 | A1 | * | 9/2002 | Yoda | ........................ G06T 5/00 382/309 |

(Continued)

FOREIGN PATENT DOCUMENTS

| JP | 4-134316 A | 5/1992 |
| JP | 07000360 A | 1/1995 |

(Continued)

OTHER PUBLICATIONS

Japanese Office Action dated Jan. 6, 2015, issued in counterpart Japanese Application No. 2011-085435.

*Primary Examiner* — David Harvey
(74) *Attorney, Agent, or Firm* — Holtz, Holtz & Volek PC

(57) ABSTRACT

An endoscope apparatus includes an imaging section, a selection section, and a shake correction section. The imaging section includes an imaging optical system and an imaging element, and captures images. The selection section selects shake correction parameter information from a plurality of pieces of shake correction parameter information based on the observation state of the imaging section. The shake correction section performs a shake correction process on the captured images based on the shake correction parameter information selected by the selection section.

11 Claims, 19 Drawing Sheets

(56) References Cited

U.S. PATENT DOCUMENTS

| | | | |
|---|---|---|---|
| 2007/0276184 A1* | 11/2007 | Okawa | A61B 1/04 600/117 |
| 2008/0043112 A1* | 2/2008 | Nikkanen | G03B 7/097 348/217.1 |
| 2008/0143827 A1* | 6/2008 | Yoshizumi | A61B 1/00059 348/65 |
| 2008/0246848 A1* | 10/2008 | Tsubaki | G06T 7/20 348/208.4 |
| 2008/0303927 A1* | 12/2008 | Khanh | H04N 5/2258 348/262 |
| 2009/0051777 A1* | 2/2009 | Lee | H04N 5/23248 348/208.99 |
| 2011/0237894 A1* | 9/2011 | Ozawa | A61B 1/043 600/168 |

FOREIGN PATENT DOCUMENTS

| | | | |
|---|---|---|---|
| JP | 02000078459 A | * | 3/2000 |
| JP | 2004230061 A | | 8/2004 |
| JP | 02006050678 A | * | 2/2006 |
| JP | 2009165553 A | | 7/2009 |
| JP | 2011027911 A | | 2/2011 |

* cited by examiner

FIG. 5

| IMAGING SECTION ID | IMAGE SIZE | IMAGING METHOD | SHAKE CORRECTION ID | SIZE OF BLOCK AREA | SIZE OF DETECTION AREA | SHAKE CORRECTION METHOD |
|---|---|---|---|---|---|---|
| 1 | 256 × 256 | PROGRESSIVE | 1 | 8 × 8 | 16 × 16 | METHOD 1 |
| 2 | 1024 × 1024 | PROGRESSIVE | 2 | 32 × 32 | 64 × 64 | METHOD 1 |
| 3 | 256 × 256 | INTERLACE | 3 | 8 × 8 | 16 × 16 | METHOD 2 |

FIG. 10

ENDOSCOPE APPARATUS AND SHAKE CORRECTION PROCESSING METHOD

Japanese Patent Application No. 2011-085435 filed on Apr. 7, 2011, is hereby incorporated by reference in its entirety.

BACKGROUND

The present invention relates to an endoscope apparatus, a shake correction method, and the like.

When performing a medical examination or treatment on an internal organ using a medical endoscope apparatus, a captured image may be blurred due to the operation (e.g., insertion, removal, or rotation) of the endoscopic scope, spontaneous peristalsis in the internal organ, and the like.

For example, JP-A-4-134316 discloses a method that detects the moving (motion) amount of object images using captured images, detects the amount of a shake corresponding to the moving amount using a mechanical vibration sensor, and calculates the moving speed of the object based on the moving amount and the amount of a shake to correct a shake between the images.

SUMMARY

According to one aspect of the invention, there is provided an endoscope apparatus including: an imaging section that includes an imaging optical system and an imaging element, and captures images; a selection section that selects shake correction parameter information from a plurality of pieces of shake correction parameter information based on an observation state of the imaging section; and a shake correction section that performs a shake correction process on the captured images based on the shake correction parameter information selected by the selection section.

According to another aspect of the invention, there is provided a shake correction method including: capturing images; selecting shake correction parameter information from a plurality of pieces of shake correction parameter information based on an observation state of the imaging section; and performing a shake correction process on the captured images based on the selected shake correction parameter information.

BRIEF DESCRIPTION OF THE DRAWINGS

FIG. 5 illustrates an example of a table.

FIG. 10 illustrates an example of image signals acquired using a two-chip imaging element.

DESCRIPTION OF EXEMPLARY EMBODIMENTS

Exemplary embodiments of the invention are described below. Note that the following exemplary embodiments do not in any way limit the scope of the invention laid out in the claims. Note also that all elements of the following exemplary embodiments should not necessarily be taken as essential elements of the invention.

1. First Embodiment 1.1. Endoscope Apparatus

Figure 1:
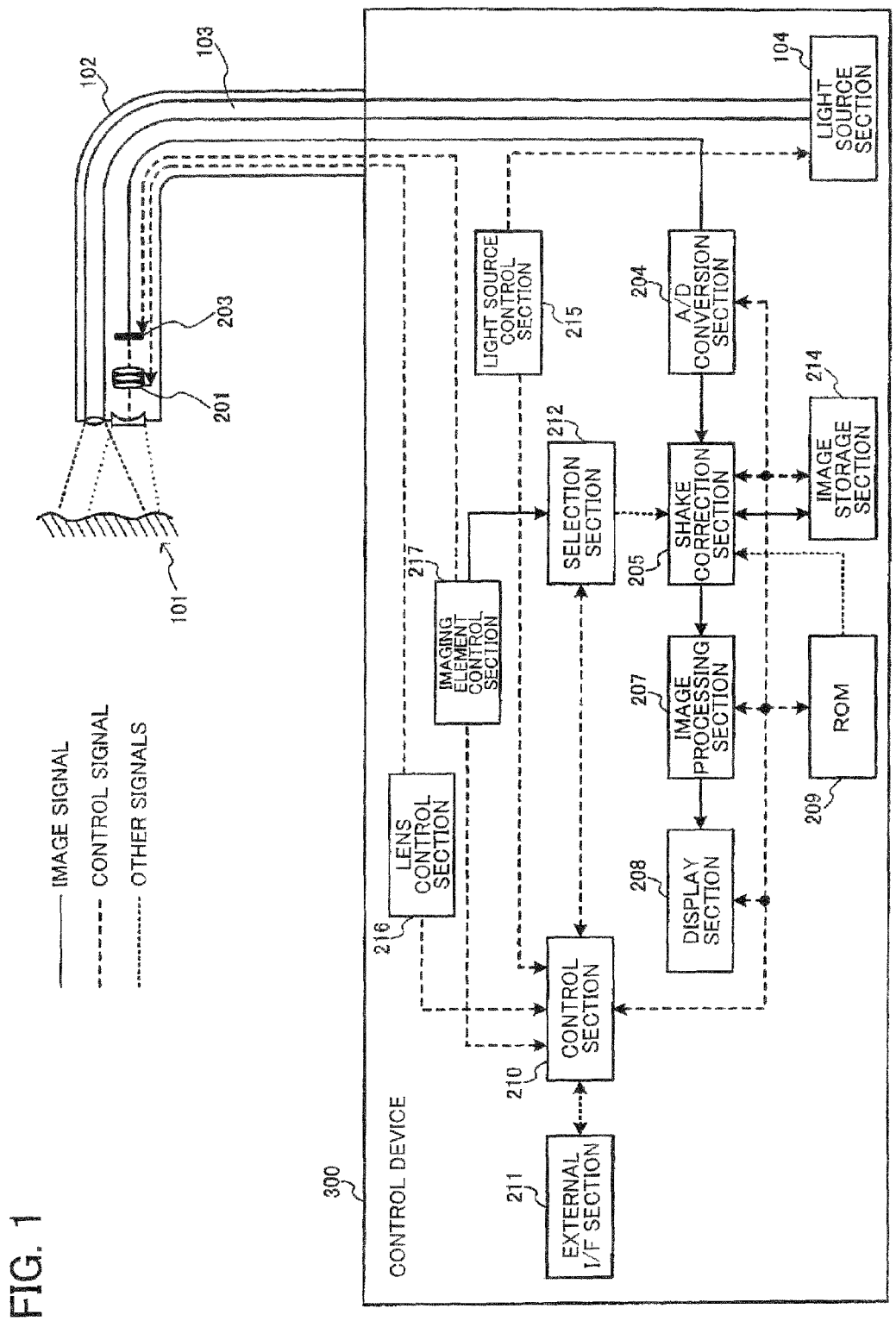
FIG. 1 illustrates a first configuration example of an endoscope apparatus according to one embodiment of the invention.

FIG. 1 illustrates a first configuration example of an endoscope apparatus according to a first embodiment of the invention. The endoscope apparatus includes a control device 300 (processor section) and an imaging section 102 (insertion section).

The imaging section 102 images (captures) an object inside a body cavity, (e.g., digestive tract). The imaging section 102 includes a light guide 103, a lens system 201, and an imaging element 203.

The control device 300 controls the endoscope apparatus, and performs image processing. The control device 300 includes a light source section 104, an A/D conversion section 204, a shake correction section 205, an image processing section 207, a display section 208, a ROM 209, a selection section 212, an image storage section 214, a light source control section 215, a lens control section 216, an imaging element control section 217, a control section 210, and an external I/F section 211.

The A/D conversion section 204 is connected to the display section 208 via the shake correction section 205 and the image processing section 207. The light source control section 215 is connected to the light source section 104. The lens control section 216 is connected to the lens system 201. The imaging element control section 217 is connected to the imaging element 203. The imaging element control section 217 is connected to the selection section 212. The selection section 212 is connected to the shake correction section 205. The ROM 209 is connected to the shake correction section 205. The image storage section 214 is bidirectionally connected to the shake correction section 205. The light source section 104 is connected to the rear end of the light guide 103. Light emitted from the light source section 104 reaches the end of the imaging section 102 via the light guide 103, and is applied to an object 101. The control device 210 is bidirectionally connected to the A/D conversion section 204, the shake correction section 205, the image processing section 207, the display section 208, the ROM 209, the selection section 212, the image storage section 214, the light source control section 215, the lens control section 216, the imaging element control section 217, and the external I/F section 211.

The imaging section 102 can be removed from the control device 300. The doctor (observer or operator) selects the desired scope from a plurality of scopes (imaging sections 102) depending on the objective, attaches the selected scope to the control device 300, and performs a medical examination or treatment.

Since the endoscope apparatus is applied to an endoscopic examination or treatment, the imaging section 102 has an elongated shape and can be curved so that the imaging section 102 can be inserted into a body. Light emitted from the light source section 104 is applied to the object 101 via the light guide 103 that can be curved. The lens system 201 is disposed on the end of the imaging section 102, and reflected light from the object 101 enters the imaging element 203 via the lens system 201. An analog image signal output from the imaging element 203 is transmitted to the A/D conversion section 204.

The A/D conversion section 204 converts the analog image signal transmitted from the imaging element 203 into a digital image signal (hereinafter referred to as "captured image"), and transmits the captured image to the shake correction section 205.

The shake correction section 205 performs a shake correction process on the captured image (image signal) transmitted from the A/D conversion section 204. Specifically, the shake correction section 205 performs an electronic shake correction process that corrects a shake that occurs between frames. More specifically, the shake correction section 205 cancels the motion of the object between a first-frame captured image and a second-frame captured image among a series of moving images by performing image processing.

The image processing section 207 performs image processing (e.g. known image processing) on the image transmitted from the shake correction section 205 under control of the control section 210. For example, the image processing section 207 performs a white balance process, a color management process, a tone conversion process, and the like. The image processing section 207 transmits the resulting RGB image to the display section 208. The display section 208 displays the RGB image.

The control section 210 controls each section of the endoscope apparatus. The external I/F section 211 receives operation information input by the doctor, and outputs the operation information to the control section 210.

The lens control section 216 changes the focal length of the lens system 201. For example, the lens control section 216 brings the imaging section 102 closer to the object 101 during zoom observation (imaging) as compared with normal observation (imaging). In this case, the lens control section 216 controls the focal length to be shorter than that during normal observation.

The imaging element control section 217 controls the imaging element 203. For example, the imaging element control section 217 controls the exposure time, the frame rate, the exposure timing, the readout timing, and the like.

The light source control section 215 controls the light source section 104. For example, the light source control section 215 controls the brightness of illumination light so that the exposure of the captured image is optimum.

1.2. Selection Section

Figure 2:
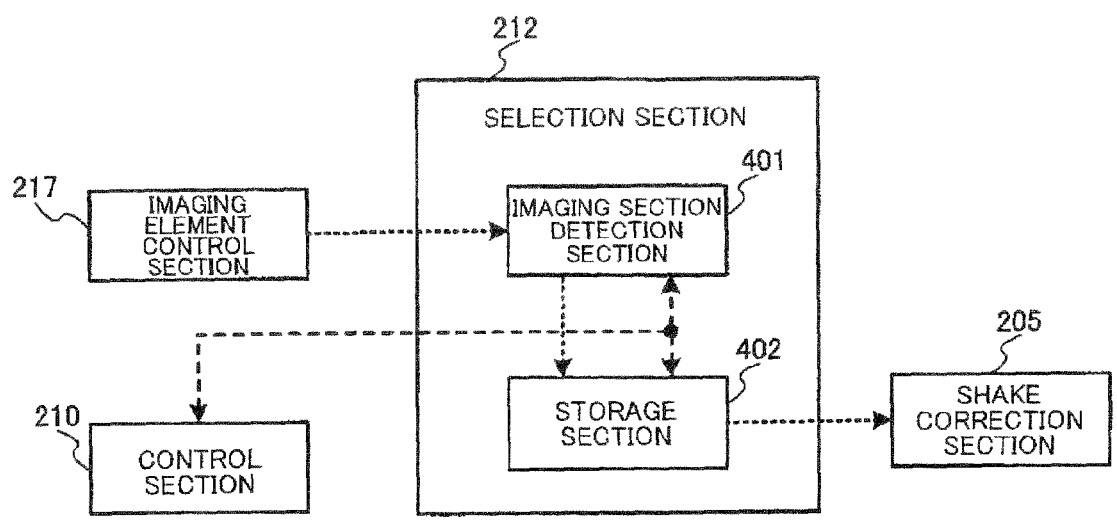
FIG. 2 illustrates a first specific configuration example of a selection section.

FIG. 2 illustrates a first specific configuration example of the selection section. As illustrated in FIG. 2, the selection section 212 includes an imaging section detection section 401 and a storage section 402 (recording section). The imaging section detection section 401 is bidirectionally connected to the storage section 402. The imaging section detection section 401 is connected to the shake correction section 205. The control section 210 is bidirectionally connected to the imaging section detection section 401 and the storage section 402.

The imaging section detection section 401 detects the imaging section ID of the imaging section 102 attached to the endoscope apparatus based on information input from the imaging element control section 217. The selection section 212 reads a shake correction ID that corresponds to the imaging section ID from the storage section 402, and transmits the shake correction ID read from the storage section 402 to the shake correction section 205.

The shake correction section 205 performs the shake correction process using the captured image transmitted from the A/D conversion section 204 and the shake correction ID transmitted from the selection section 212 under control of the control section 210. More specifically, the shake correction section 205 divides the captured image in the current frame transmitted from the A/D conversion section 204 and the captured image in the preceding frame transmitted from the image storage section 214 into a plurality of block areas having a given size, and detects the motion amount (e.g., motion vector) using a known template matching process. The shake correction section 205 calculates the global motion amount in the current frame by calculating the weighted average of the motion amount of each block area. The shake correction section 205 performs the shake correction process on the captured image in the current frame transmitted from the A/D conversion section 204 based on the calculated global motion amount.

More specifically, the shake correction section 205 sets a trimming area to the captured image in the current frame. The shake correction section 205 moves the trimming area by the calculated global motion amount, and trims and outputs the trimming area.

1.3. Shake Correction Section

Figure 3:
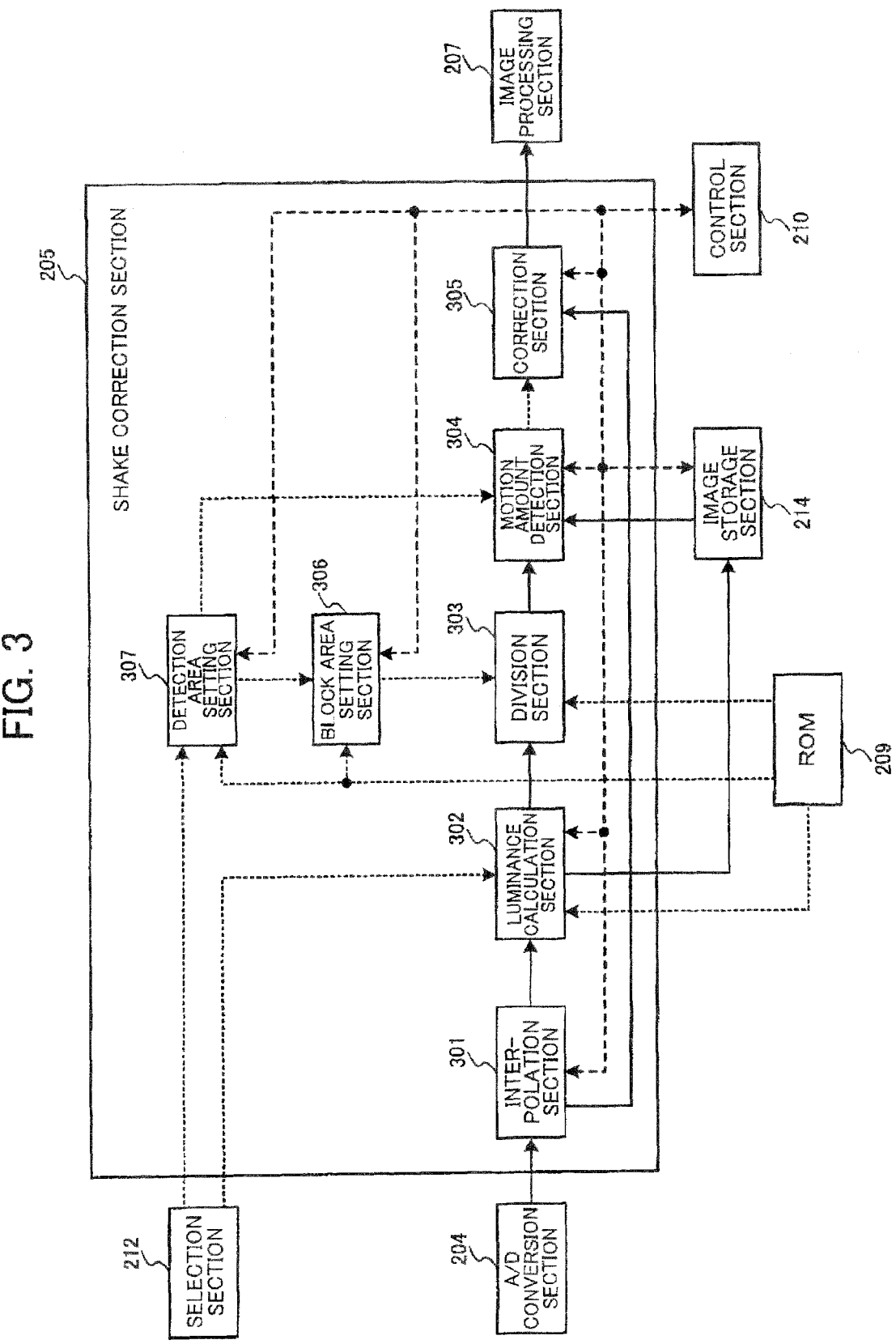
FIG. 3 illustrates a first specific configuration example of a shake correction section.

FIG. 3 illustrates a first specific configuration example of the shake correction section. The shake correction section 205 includes an interpolation section 301, a luminance calculation section 302, a division section 303, a motion amount detection section 304, a correction section 305, a block area setting section 306 (block area determination section), and a detection area setting section 307 (detection area determination section).

The selection section 212 is connected to the luminance calculation section 302 and the detection area setting section 307. The A/D conversion section 204 is connected to the image processing section 207 via the interpolation section 301, the luminance calculation section 302, the division section 303, the motion amount detection section 304, and the correction section 305. The ROM 209 is connected to the luminance calculation section 302, the division section 303, the block area setting section 306, and the detection area setting section 307. The block area setting section 306 is connected to the division section 303. The detection area setting section 307 is connected to the block area setting section 306 and the motion amount detection section 304. The luminance calculation section 302 is connected to the image storage section 214. The interpolation section 301 is connected to the luminance calculation section 302 and the correction section 305. The image storage section 214 is connected to the motion amount detection section 304. The control section 210 is bidirectionally connected to the interpolation section 301, the luminance calculation section 302, the division section 303, the motion amount detection section 304, the correction section 305, the block area setting section 306, and the detection area setting section 307.

The imaging element 203 is a single-chip imaging element that acquires a primary-color image, for example. In this case, the interpolation section 301 performs a known Bayer interpolation process (i.e., a process that converts a Bayer image into an RGB image) on the primary-color captured image in the current frame transmitted from the A/D conversion section 204 under control of the control section 210. The interpolation section 301 transmits the resulting RGB image to the luminance calculation section 302.

The luminance calculation section 302 calculates the luminance Y(x, y) using the RGB image (see the following expression (1)) under control of the control section 210. The luminance calculation section 302 transmits the calculated luminance Y(x, y) to the division section 303 and the image storage section 214. The luminance image (i.e., an image generated using the luminance) stored in the image storage section 214 is used as the luminance image in the preceding frame when performing the shake correction process on the luminance image in the next frame. More specifically, the oldest luminance image stored in the image storage section 214 is updated (i.e., the luminance image in the current frame is stored) each time a new luminance image has been acquired.

$$Y(x,y)=a1*R(x,y)+b1*G(x,y)+c1*B(x,y) \qquad (1)$$

where, x and y are respectively the horizontal coordinate value and the vertical coordinate value that correspond to each pixel of the image. For example, the horizontal axis is parallel to the horizontal scan line, and the vertical axis is orthogonal to the horizontal axis. Y(x, y) is the luminance, and R(x, y). G(x, y), and B(x, y) are RGB pixel values. a1, b1, and c1 are given coefficients used to calculate the luminance.

Although an example in which the luminance is calculated by the expression (1) has been described above, the G image captured using the G filter may be used as the luminance image.

The detection area setting section 307 sets the size of a motion amount detection area. More specifically, the detection area setting section 307 reads (extracts) the size of the detection area that corresponds to the shake correction ID transmitted from the selection section 212 from the ROM 209, and transmits the size of the detection area read from the ROM 209 to the motion amount detection section 304. The detection area setting section 307 transmits the shake correction ID transmitted from the selection section 212 to the block area setting section 306 under control of the control section 210.

The block area setting section 306 sets the size of the block area. More specifically, the block area setting section 306 reads the size of the block area that corresponds to the shake correction ID transmitted from the detection area setting section 307 from the ROM 209, and transmits the size of the block area read from the ROM 209 to the division section 303.

The division section 303 divides the luminance image in the current frame transmitted from the luminance calculation section 302 into a plurality of block areas based on block area size information transmitted from the block area setting section 306. The division section 303 transmits the divided luminance image to the motion amount detection section 304.

The motion amount detection section 304 performs a known template matching process (SSD or SAD) on the luminance image in the preceding frame transmitted from the image storage section 214 using the divided luminance image in the current frame transmitted from the division section 303 based on detection area size information transmitted from the detection area setting section 307.

The correction section 305 performs a known shake correction process on the captured image in the current frame based on matching information transmitted from the motion amount detection section 304, and transmits the resulting image to the image processing section 207.

Figure 4:
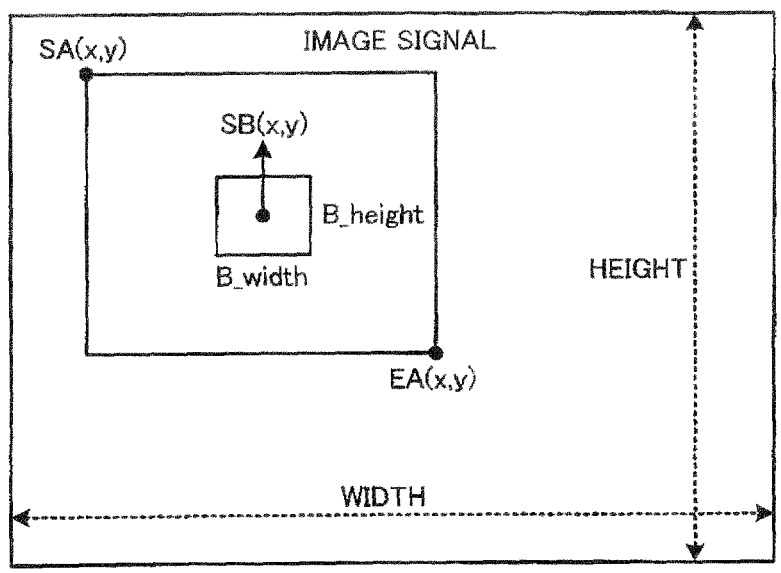
FIG. 4 illustrates an example of a template matching process.

FIG. 4 illustrates an example of the template matching process. In FIG. 4, the image size is indicated by the height HEIGHT and the width WIDTH. The division section 303 divides the luminance image in the current frame transmitted from the luminance calculation section 302 into a plurality of block areas based on the block area size information. The block area size information includes the height B_height and the width B_width of the block area.

The motion amount detection section 304 detects the motion amount of the block area using a block center point SB(x, y) as a block representative point under control of the control section 210. In this case, the motion amount detection section 304 performs the template matching process on an attention block area and the detection area. The term "attention block area" used herein refers to the processing target block area among the plurality of block areas that are sequentially subjected to the template matching process. The detection area is set based on the detection area size information transmitted from the detection area setting section 307. The detection area size information includes the start coordinates SA(x, y) and the end coordinates EA(x, y) of the detection area. The height and the width of the detection area are respectively larger than the height and the width of the block area. When the motion amount detection section 304 has performed the template matching process on each block area, the motion amount detection section 304 calculates the global motion amount in the current frame by calculating the weighted average of the motion amount of each block area, and transmits the calculated global motion amount to the correction section 305.

The term "motion amount" used herein refers to the motion amount of the object between the captured images (e.g., the motion direction or the motion distance of the object between the captured images). The motion amount may be the motion amount of the object between two frames, or may be the motion amount of the object over a plurality of frames. For example, the motion amount is the motion vector of the object between the captured images.

The correction section 305 performs a known shake correction process on the captured image in the current frame transmitted from the interpolation section 301 based on the global motion amount transmitted from the motion amount detection section 304. For example, the correction section 305 performs the shake correction process on each RGB pixel (R(I, J), G(I, J), and B(I, J), I is the horizontal coordinate value of each pixel, and J is the vertical coordinate value of each pixel) of the captured image in the current frame based on the global motion amount (direction and distance) in the current frame (see the following expression (2)).

$$I'=I+\text{move}X,$$

$$J'=J+\text{move}Y \quad (2)$$

where, I' is the horizontal coordinate value after the shake correction process, and J' is the vertical coordinate value after the shake correction process. moveX is the horizontal global motion amount between the captured images in the current frame. The global motion amount moveX is indicated by the number of pixels by which the object has moved in the horizontal direction. The global motion amount moveX is indicated by a positive number of pixels when the object has moved in the positive direction (e.g., rightward direction) relative to the coordinate value I, and is indicated by a negative number of pixels when the object has moved in the negative direction (e.g., leftward direction) relative to the coordinate value I. The global motion amount moveY is indicated by the number of pixels by which the object has moved in the vertical direction. The global motion amount moveY is indicated by a positive number of pixels when the object has moved in the positive direction (e.g., downward direction) relative to the coordinate value J, and is indicated by a negative number of pixels when the object has moved in the negative direction (e.g., upward direction) relative to the coordinate value J.

The first embodiment is characterized in that a different shake correction process is performed corresponding to the size of the image captured by the imaging element 203. For example, images that have been captured at the same angle of view, but captured by imaging elements that differ in image size, differ in resolution (i.e., are observed in a different way) depending on the image size. The resolution of the captured image having a large size is higher than that of the captured image having a small size. Therefore, it is likely that the motion amount detection accuracy differs due to the difference in resolution when detecting the motion amount using the same detection area size and the same block area size under conditions where the angle of view is the same, but the image size differs.

In order to solve this problem, the first embodiment sets the size of the detection area and the size of the block area used to detect the motion amount corresponding to the size of the captured image output from the imaging element 203. More specifically, the size of the detection area and the size of the block area are set in proportion to the image size. For example, when capturing images at the same angle of view, the size of the block area is set to 32×32 pixels, and the size of the detection area is set to 64×64 pixels when the image size is 1024×1024 pixels. The size of the block area is set to 8×8 pixels, and the size of the detection area is set to 16×16 pixels when the image size is 256×256 pixels. This makes it possible to detect the motion amount at almost the same angle of view, so that the motion amount detection accuracy can be made equal.

More specifically, the relationship between the imaging section ID and the image size and the relationship between the imaging section ID and the shake correction ID are provided in a tabular form (see FIG. 5), and stored in the storage section 402 (see FIG. 2). The relationship between the shake correction ID and the size of the block area and the relationship between the shake correction ID and the size of the detection area are also provided in a tabular form, and stored in the ROM 209 (see FIG. 1).

The detection accuracy when detecting the motion amount between the captured images can be improved by thus adaptively setting the size of the detection area and the size of the block area corresponding to the image size. This makes it possible to improve the shake correction accuracy, and improve the diagnostic capability.

1.4. First Modification

A captured image having a small size has a resolution lower than that of a captured image having a large size when the angle of view is the same. As a result, the motion amount may not be correctly detected even if the size of the detection area and the size of the block area are changed adaptively. According to a first modification of the first embodiment, edge information is detected from an image before detecting the motion amount, and an enhancement process is performed using the detected edge information. The details of the first modification are described below.

Figure 6:
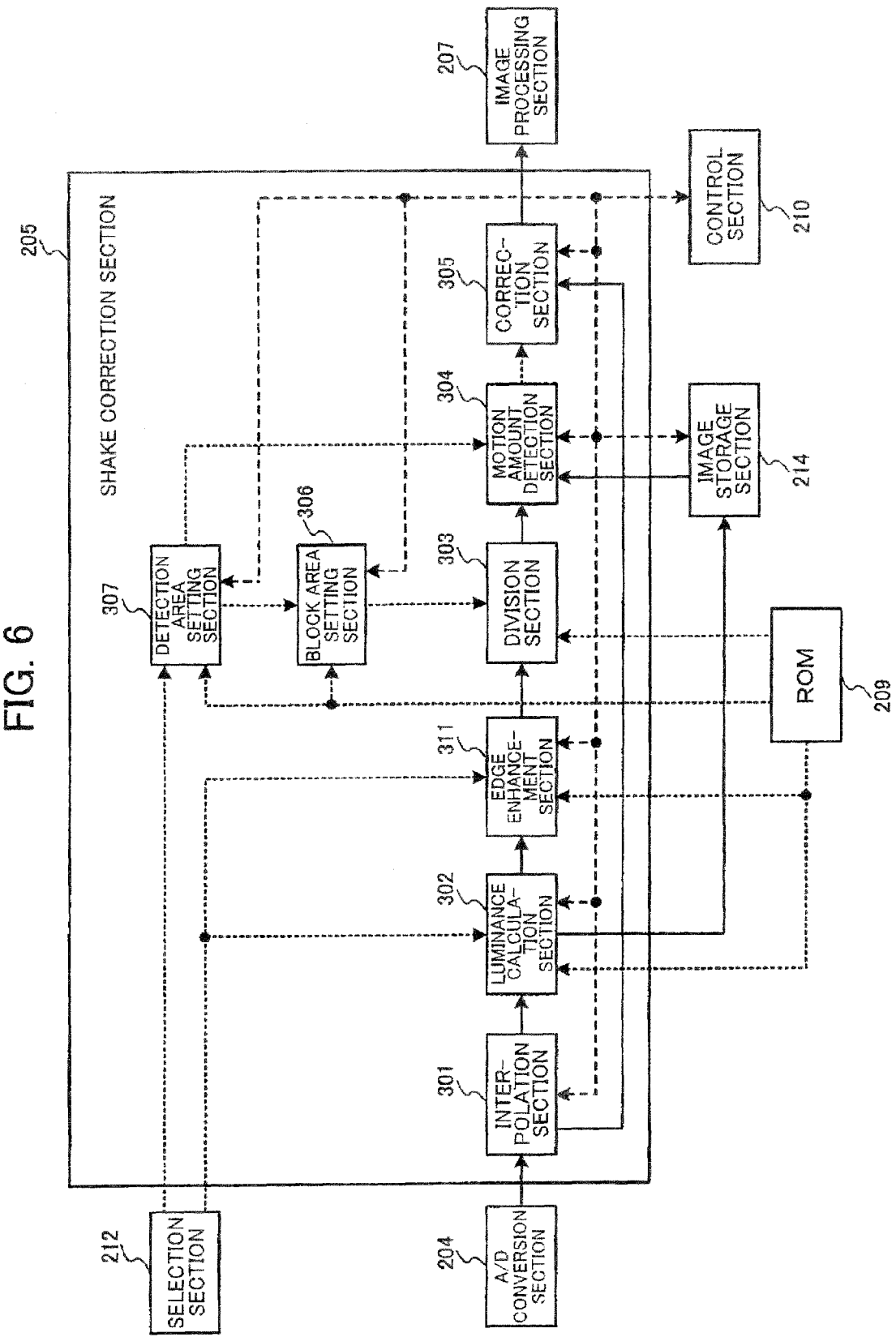
FIG. 6 illustrates a second specific configuration example of a shake correction section.

FIG. 6 illustrates a second specific configuration example of the shake correction section. As illustrated in FIG. 6, the shake correction section 205 includes an interpolation section 301, a luminance calculation section 302, an edge enhancement section 311, a division section 303, a motion amount detection section 304, a correction section 305, a block area setting section 306, and a detection area setting section 307.

The selection section 212 is connected to the luminance calculation section 302, the edge enhancement section 311, and the detection area setting section 307. The A/D conversion section 204 is connected to the image processing section 207 via the interpolation section 301, the luminance calculation section 302, the edge enhancement section 311, the division section 303, the motion amount detection section 304, and the correction section 305. The ROM 209 is connected to the luminance calculation section 302, the edge enhancement section 311, the division section 303, the block area setting section 306, and the detection area setting section 307. The interpolation section 301 is connected to the luminance calculation section 302 and the correction section 305. The detection area setting section 307 is connected to the division section 303 via the block area setting section 306. The detection area setting section 307 is connected to the motion amount detection section 304. The luminance calculation section 302 is connected to the image storage section 214. The image storage section 214 is connected to the motion amount detection section 304. The control section 210 is bidirectionally connected to the interpolation section 301, the luminance calculation section 302, the edge enhancement section 311, the division section 303, the motion amount detection section 304, the correction section 305, the block area setting section 306, and the detection area setting section 307.

Note that the following description focuses on the differences from the first embodiment, and description of the same elements as those illustrated in FIG. 3 is appropriately omitted.

Figure 7:
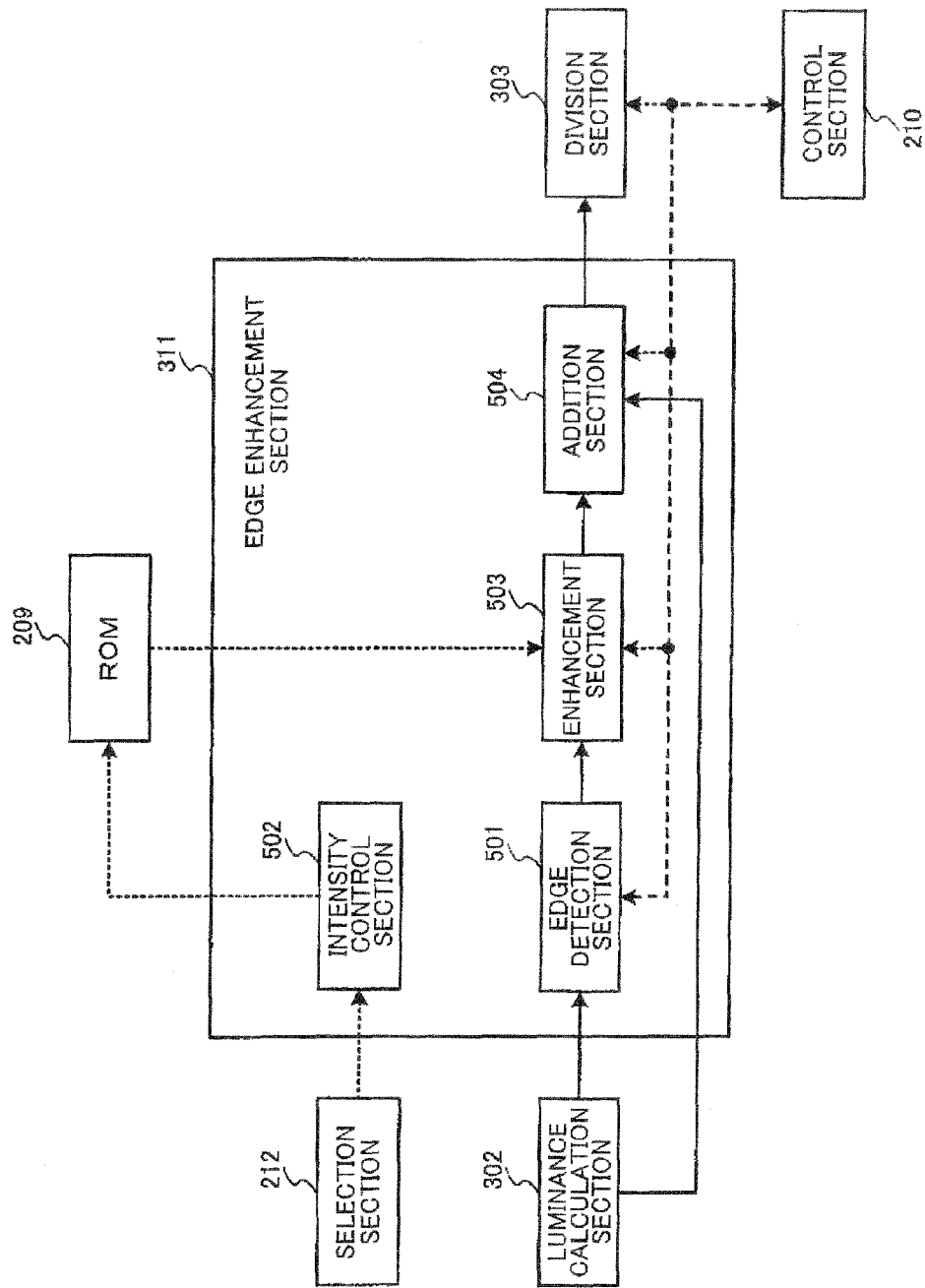
FIG. 7 illustrates a specific configuration example of an edge enhancement section.

FIG. 7 illustrates a specific configuration example of the edge enhancement section. As illustrated in FIG. 7, the edge enhancement section 311 includes an edge detection section 501, an intensity (degree) control section 502, an enhancement section 503, and an addition section 504.

The luminance calculation section 302 is connected to the division section 303 via the edge detection section 501, the enhancement section 503, and the addition section 504. The selection section 212 is connected to the intensity control section 502. The ROM 209 is connected to the enhancement section 503 via the intensity control section 502. The luminance calculation section 302 is connected to the addition section 504. The control section 210 is bidirectionally connected to the edge detection section 501, the intensity control section 502, the enhancement section 503, and the addition section 504.

The edge detection section 501 performs a known Laplacian filter process on the luminance image in the current frame transmitted from the luminance calculation section 302 and the luminance image in the preceding frame to detect edge data, and transmits the edge data to the enhancement section 503.

The intensity control section 502 reads an intensity (degree) weighting coefficient that corresponds to the shake correction ID transmitted from the selection section 212 from the ROM 209, and transmits the intensity weighting coefficient to the edge enhancement section 311. The edge enhancement intensity weighting coefficient is stored in the ROM 209 in advance. According to the first modification, a different intensity weighting coefficient is set corresponding to the shake correction ID.

More specifically, since a captured image having a small size has a resolution lower than that of a captured image having a large size when the angle of view is the same, the intensity control section 502 sets the intensity weighting coefficient corresponding to the image size. For example, the intensity control section 502 increases the intensity weighting coefficient as the image size increases.

The enhancement section 503 performs the enhancement process on the edge data using the intensity weighting coefficient, and transmits the resulting (enhanced) edge data to the addition section 504. The addition section 504 adds the edge data transmitted from the enhancement section 503 to the luminance image transmitted from the luminance calculation section 302, and transmits the resulting luminance image to the division section 303.

Note that the intensity weighting coefficient may be set corresponding to the MTF of the lens system 201. Specifically, images that have been captured at the same angle of view using different imaging elements that correspond to the same image size differ in resolution depending on the MTF of the lens system 201. In this case, the accuracy of the template matching process can be improved by adaptively adjusting the intensity (degree) of the edge enhancement process depending on (corresponding to) the MTF of the lens system 201. For example, when the MTF of the lens system 201 is low, it is necessary to increase the intensity weighting coefficient since the resolution of the captured image is low. When the MTF of the lens system 201 is high, the intensity weighting coefficient is reduced since the resolution of the captured image is high.

The contrast of the captured image can be improved by thus adaptively adjusting the intensity of the edge enhancement process or the MTF depending on (corresponding to) the image size. This makes it possible to improve the motion amount detection accuracy.

1.5. Second Modification

A second modification of the first embodiment is described below. According to the second modification, the motion amount detection method is adaptively changed depending on the sensor configuration of the imaging element 203. For example, the shake correction method is switched between the method 1 and the method 2 depending on whether the imaging method is the progressive method or the interlace method (see FIG. 5).

Figure 8:
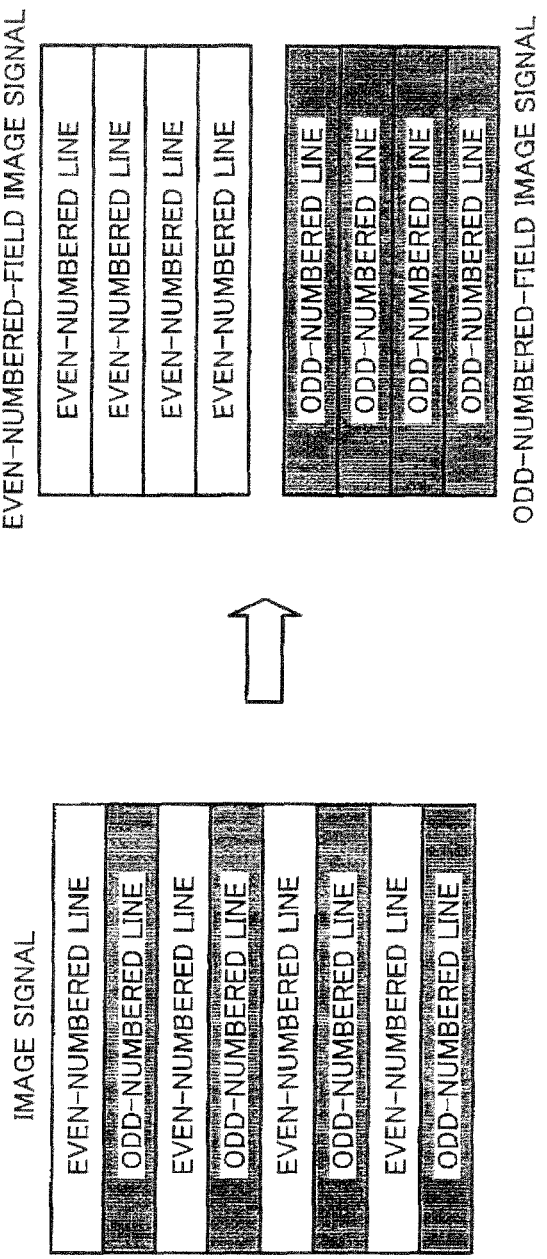
FIG. 8 illustrates a configuration example of interlaced complementary color image signals.

A case where the imaging element 203 is an interlaced complementary color single-chip imaging element is described below. FIG. 8 illustrates a configuration example of interlaced complementary color (Mg, G, Cy, Ye) image signals. An image captured by the imaging element 203 includes odd-numbered-field image signals (odd-numbered lines) and even-numbered-field image signals (even-numbered lines). The odd-numbered-field image signals and the even-numbered-field image signals are alternately input to the A/D conversion section 204 in time series. The interpolation section 301 performs a known interpolation process on the odd-numbered-field image signals and the even-numbered-field image signals under control of the control section 210. The luminance calculation section 302 converts the odd-numbered-field image signals and the even-numbered-field image signals into luminance signals and color difference signals.

Figure 9:
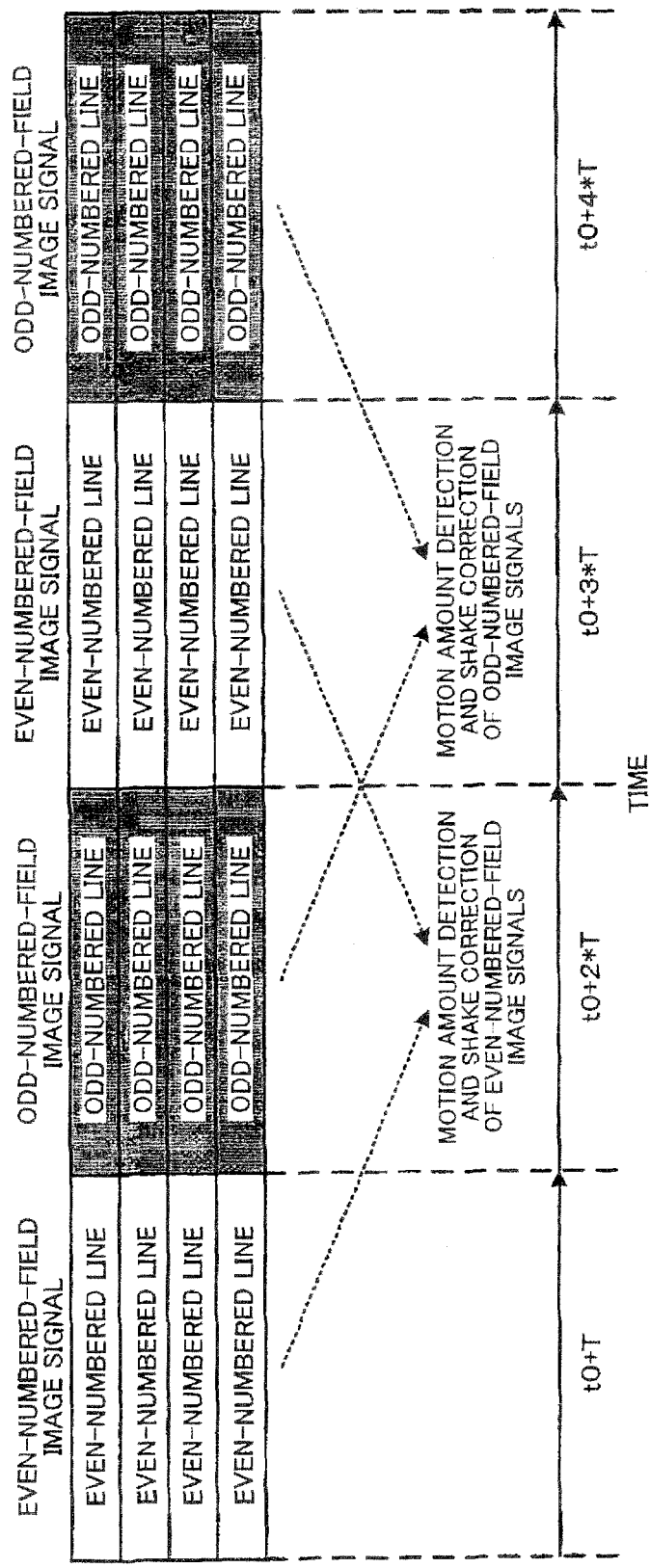
FIG. 9 is a view illustrating the relationship between a motion amount detection process and a shake correction process when using an interlace method.

As illustrated in FIG. 9, the odd-numbered-field image signals and the even-numbered-field image signals are alternately acquired in time series in a cycle T. The motion amount detection section 304 alternately detects the motion amount of the object in the odd-numbered field and the motion amount of the object in the even-numbered field in time series. More specifically, the motion amount detection section 304 detects the motion amount of the object in the odd-numbered field from the luminance signal in the current odd-numbered field and the luminance signal in the preceding odd-numbered field, and detects the motion amount of the object in the even-numbered field from the luminance signal in the current even-numbered field and the luminance signal in the preceding even-numbered field. The shake correction section 205 performs the shake correction process on the current odd-numbered-field image signals using the motion amount of the object in the odd-numbered field, and performs the shake correction process on the current even-numbered-field image signals using the motion amount of the object in the even-numbered field.

A case where the imaging element 203 is an RGB three-chip imaging element is described below. In this case, RGB pixel values are acquired corresponding to each pixel. The luminance calculation section 302 calculates the luminance $Y(x, y)$ of each pixel using the pixel values (see the expression (1)). The motion amount detection section 304 calculates the motion amount using the calculated luminance, and the shake correction section 205 performs the shake correction process using the calculated motion amount. Note that the motion amount may be calculated using the G pixel value of each pixel as the luminance, and the shake correction process may be performed using the calculated motion amount.

Figure 10:
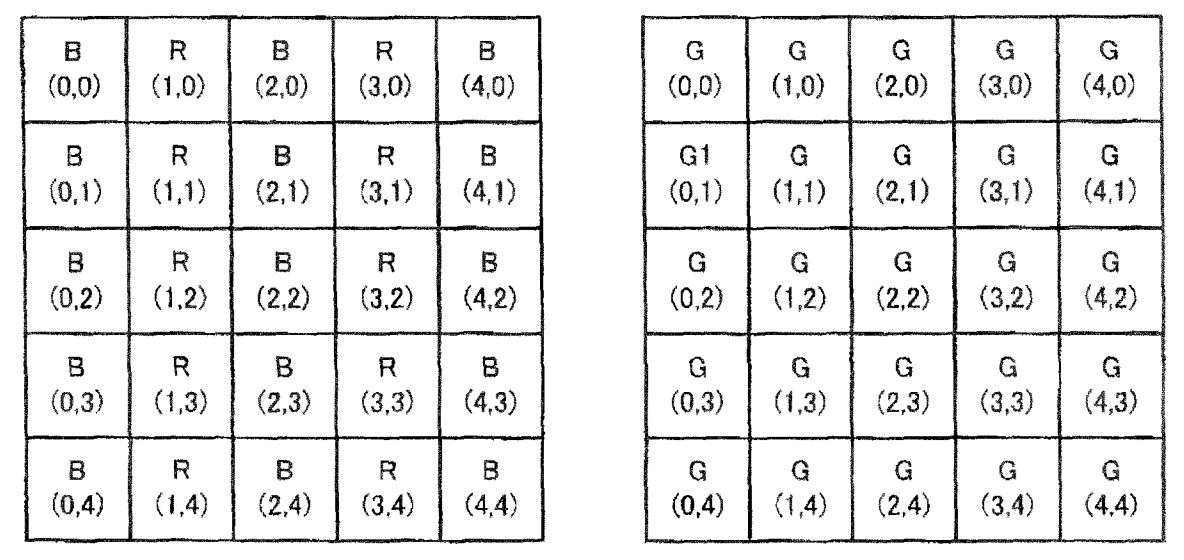

A case where the imaging element 203 is a two-chip imaging element is described below. FIG. 10 illustrates an example of image signals acquired using the two-chip imaging element. As illustrated in FIG. 10, an image captured by a first imaging element has R pixel values and B pixel values (R image signals and B image signals). The R pixels and the B pixels are arranged every two columns. An image (G image captured by a second imaging element has G pixel values (G image signals) over the entire image. In this case, the interpolation section 301 generates an R image having R pixel values over the entire image and a B image having B pixel values over the entire image by performing an interpolation process shown by the following expression (3) under control of the control section 210.

$$R(x,y)=(R(x-1,y)+R(x+1,y))/2,$$

$$B(x+1,y)=(B(x,y)+B(x+2,y))/2 \qquad (3)$$

where, x and y are respectively the horizontal coordinate value and the vertical coordinate value that correspond to each pixel of the captured image. R(x, y) and B(x+1, y) are pixel values obtained by the interpolation process. R(x−1, y), R(x+1, y), B(x, y), and B(x+2, y) are pixel values before performing the interpolation process.

When performing the shake correction process using the endoscope apparatus, the occurrence frequency and the degree of shake may differ depending on the characteristics of the imaging section and the observation state (e.g. the observation (imaging) mode and the skill of the observer), for example.

According to the first embodiment, the endoscope apparatus includes the imaging section 102, the selection section 212, and the shake correction section 205 (see FIG. 1). The imaging section 102 includes the imaging optical system (lens system 201) and the imaging element 203, and captures an image. The selection section 212 selects shake correction parameter information from a plurality of pieces of shake correction parameter information based on the observation state of the imaging section 102. The shake correction section 205 performs the shake correction process on the captured image based on the shake correction parameter information selected by the selection section 212.

For example, a plurality of shake correction ID are stored as the plurality of pieces of shake correction parameter information. The shake correction ID that corresponds to the observation state is selected, and an electronic shake correction process is performed using a parameter designated by the shake correction ID.

According to the above configuration, the shake correction parameter information used for the shake correction process is selected from the plurality of pieces of shake correction parameter information based on the observation state of the imaging section. The shake correction process is performed on the captured image based on the selected shake correction parameter information. This makes it possible to perform an appropriate shake correction process corresponding to the observation state. More specifically, an optimum shake correction parameter can be set corresponding to the observation state. This makes it possible to adaptively perform the shake correction process corresponding to the occurrence frequency and the degree of shake, and improve the visibility of the object. Therefore, it is possible to prevent a situation in which a lesion is missed, and reduce the burden of medical examination.

Note that the term "shake correction parameter information" used herein refers to information that designates the parameter used for the shake correction process. Parameter information that relates to shake suppression control that suppresses a shake among frames, light control that adjusts the intensity of illumination light, and the like is also appropriately referred to as the shake correction parameter information. The shake correction parameter information may be information (e.g., ID) that corresponds to the parameter, or may be the parameter.

The term "observation state" used herein refers to the imaging state or situation using the endoscope apparatus. For example, the observation state refers to the size (number of pixels) of the captured image, or the state of the captured image indicated by the MTF of the imaging optical system or the like. The observation state may be the imaging method (e.g., interlace method). The observation state may also be an observation mode such as a normal observation mode or a zoom observation mode, an observation mode such as a screening mode or a close examination mode, or an observer mode that corresponds to the skill of the doctor.

A plurality of types of imaging section 102 may be able to be removably attached to the endoscope apparatus. The selection section 212 may include the imaging section detection section 401 that detects the type of imaging section 102 attached to the endoscope apparatus, and the storage section 402 that stores the plurality of pieces of shake correction parameter information (i.e., a plurality of shake correction ID) that respectively correspond to the plurality of types of imaging section 102 (see FIG. 2). The selection section 212 may select the shake correction parameter information (shake correction ID) that corresponds to the type of imaging section 102 attached to the endoscope apparatus from the plurality of pieces of shake correction parameter information stored in the storage section 402.

More specifically, the endoscope apparatus may include the block area setting section 306, the division section 303, and the detection area setting section 307 (see FIG. 3). The block area setting section 306 may set a plurality of block areas to the captured image. The division section 303 may divide the captured image into the plurality of block areas. The detection area setting section 307 may set a motion amount detection target area within the captured image. The selection section 212 may select the shake correction parameter information that corresponds to the size of the plurality of block areas and the size of the motion amount detection target area corresponding to the size (number of pixels) of the imaging element 203 of the imaging section 102 attached to the endoscope apparatus (see FIG. 5). The motion amount detection section 304 may detect the motion amount using a block area among the plurality of block areas and the motion amount detection target area having a size (B_width, B_height, SA(x, y), and EA(x, y)) that corresponds to the shake correction parameter information selected by the selection section 212 (see FIG. 4).

This makes it possible to set an appropriate block area and an appropriate detection target area corresponding to the imaging section even when the imaging section has been exchanged. Specifically, since the number of pixels of an image differs depending on the specification of the imaging section, the size (angle of view) of each area relative to the size of the image does not become constant if the size of each area is set to the same value. According to the above configuration, the angle of view of each area can be set to be constant by adaptively setting the size of each area.

The shake correction section 205 may include the motion amount detection section 304 that detects the motion amount of the object between the captured images (see FIG. 3). The selection section 212 may select the shake correction parameter information corresponding to the imaging method of the imaging section 102 attached to the endoscope apparatus. The motion amount detection section 304 may detect the motion amount using the detection method that corresponds to the shake correction parameter information selected by the selection section 212.

The imaging method may be a single-chip interlace method, a single-chip progressive method, a two-chip imaging element method, or a three-chip imaging element method.

For example, the imaging section 102 may include a first imaging element that captures a G image, and a second imaging element that captures an R image and a B image (two-chip imaging method) (see FIG. 10). In this case, the selection section 212 may select the shake correction parameter information that detects the motion amount from the G image.

Alternatively, the imaging section 102 may include a first imaging element that captures a G image, a second imaging element that captures an R image, and a third imaging element that captures a B image (three-chip imaging method). In this case, the selection section 212 may select the shake correction parameter information that detects the motion amount from a luminance image based on the G image, the R image, and the B image.

The imaging section 102 may capture the captured image using the interlace method (see FIG. 8). In this case, the selection section 212 may select the shake correction parameter information that detects a first motion amount based on odd-numbered horizontal scan line image signals, and detects a second motion amount based on even-numbered horizontal scan line image signals (see FIG. 9). The shake correction section 205 may perform the shake correction process on the odd-numbered horizontal scan line image signals based on the first motion amount, and may perform the shake correction process on the even-numbered horizontal scan line image signals based on the second motion amount.

The imaging section 102 may capture an R image, a G image, and a B image in time series using a frame sequential method. In this case, the selection section 212 may select the shake correction parameter information that detects a first motion amount based on the R image, detects a second motion amount based on the G image, and detects a third motion amount based on the B image. The shake correction section 205 may perform the shake correction process on the R image based on the first motion amount, may perform the shake correction process on the G image based on the second motion amount, and may perform the shake correction process on the B image based on the third motion amount.

This makes it possible to perform the shake correction process using an appropriate detection method corresponding to the imaging method of the imaging section 102. Specifically, various imaging sections 102 are removably attached to the endoscope apparatus corresponding to the examination target area and the like, and the format and the characteristics of the captured image differ depending on the imaging method. According to the above configuration, the shake correction process corresponding to the format and the characteristics of the captured image can be set based on the information (e.g., imaging section ID) read from the storage section 402.

The endoscope apparatus may include the edge enhancement section 311 that performs the edge enhancement process on the captured image (see FIG. 6). The selection section 212 may select the shake correction parameter information that corresponds to a first intensity of the edge enhancement process when the imaging element 203 of the imaging section 102 attached to the endoscope apparatus has a first size, and may select the shake correction parameter information that corresponds to a second intensity of the edge enhancement process when the imaging element 203 has a second size, the second intensity being higher than the first intensity, and the second size being smaller than the first size. The edge enhancement section 311 may perform the edge enhancement process at an intensity that corresponds to the shake correction parameter information selected by the selection section 212.

This makes it possible to perform the edge enhancement process at an intensity corresponding to the size of the imaging element 203, and perform the shake correction process using the image obtained by the edge enhancement process. Therefore, the matching accuracy can be improved by the edge enhancement process even when the number of pixels of the imaging element 203 is small, and the resolution of the image signal is low, so that the shake correction accuracy can be improved.

Note that the intensity of the edge enhancement process refers to the degree of enhancement of an edge component (e.g., high-frequency component) of the original image. For example, when multiplying an edge component extracted from the original image by a coefficient, and adding the resulting edge component to the original image, the coefficient is increased as the intensity increases.

2. Second Embodiment 2.1. Configuration Example

A second embodiment of the invention is described below. In the second embodiment, the shake correction process is adaptively performed corresponding to the observer mode.

Figure 11:
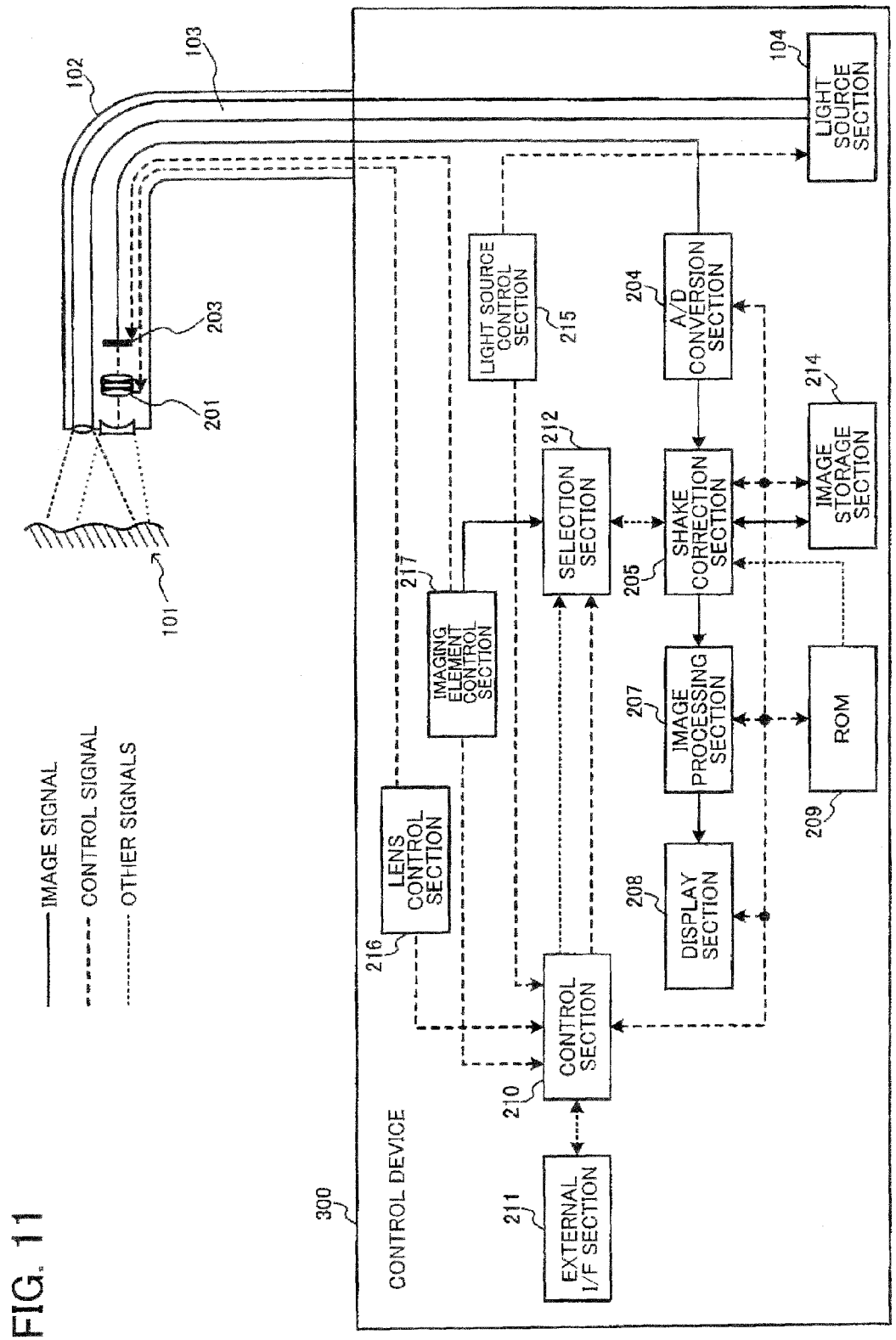
FIG. 11 illustrates a second configuration example of an endoscope apparatus.

FIG. 11 illustrates a second configuration example of the endoscope apparatus. As illustrated in FIG. 11, the endoscope apparatus includes a control device 300 and an imaging section 102. The imaging section 102 includes a light guide 103, a lens system 201, and an imaging element 203. The control device 300 includes a light source section 104, an A/D conversion section 204, a shake correction section 205, an image processing section 207, a display section 208, a ROM 209, a selection section 212, an image storage section 214, a light source control section 215, a lens control section 216, an imaging element control section 217, a control section 210, and an external I/F section 211.

The configuration of the endoscope apparatus according to the second embodiment is the same as the configuration of the endoscope apparatus according to the first embodiment, except for the selection section 212. The following description focuses on the differences from the first embodiment, and description of the same elements as those described in connection with the first embodiment is appropriately omitted.

When the end of the imaging section moves randomly, the shake of the captured images can be suppressed by performing the shake correction process. However, when the end of the imaging section moves in a constant direction due to the operation of the doctor, for example, a delay in the display image may increase due to the shake correction process.

A medical examination or treatment on an internal organ using a medical endoscope apparatus includes screening observation that searches for a lesion area, and close observation that closely examines a lesion area or a suspected lesion area. When an experienced doctor performs screening observation (examination), the probability that a lesion area is missed is low since the amount of a shake due to the operation (e.g., insertion, removal, or rotation) of the endoscopic scope is small. When an experienced doctor performs close observation (examination), a lesion area can be determined accurately and quickly since an experienced doctor can focus on the attention area and minimize the amount of a shake. However, when an inexperienced doctor performs screening observation (examination), the probability that a lesion area is missed increases since the amount of a shake due to the operation of the endoscopic scope is large. When an inexperienced doctor performs close observation (examination), it is likely that diagnosis takes time since an inexperienced doctor cannot focus on the attention area and effectively suppress a shake.

According to the second embodiment, a different shake correction process is performed depending on (corresponding to) the skill (experience) of the doctor. More specifically, when an experienced (skilled) doctor operates the endoscopic scope, the motion amount detection period is reduced so that the captured image is displayed without a delay since the amount of a shake due to the operation of the endoscopic scope is small. On the other hand, when an inexperienced doctor operates the endoscopic scope, the motion amount detection period is increased even if the captured image is displayed with a delay since the amount of a shake due to the operation of the endoscopic scope is large.

Figure 12:
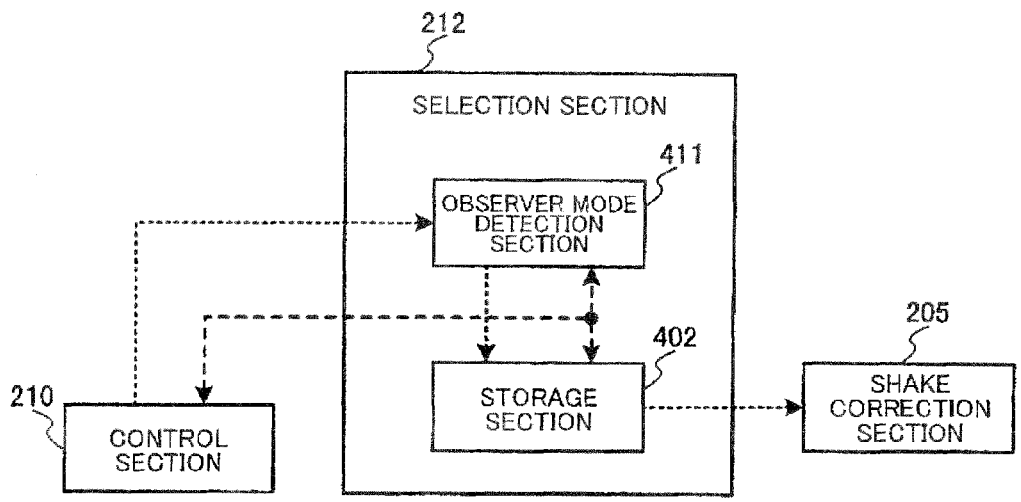
FIG. 12 illustrates a second specific configuration example of a selection section.

FIG. 12 illustrates a second specific configuration example of the selection section. As illustrated in FIG. 12, the selection section 212 includes an observer mode detection section 411 and a storage section 402. The observer mode detection section 411 is connected to the shake correction section 205 via the storage section 402. The control section 210 is bidirectionally connected to the observer mode detection section 411 and the storage section 402.

A doctor ID assigned to each doctor and a shake correction ID that corresponds to the experience of each doctor are stored in the storage section 402 in advance. The doctor ID and the shake correction ID have a one-to-one relationship (or a plurality of doctor ID correspond to one shake correction ID). The shake correction ID that corresponds to the doctor ID can be appropriately registered or revised corresponding to the doctor's medical examination experience.

The doctor inputs his doctor ID via the external I/F section 211 when performing a medical examination. The observer mode detection section 411 reads the shake correction ID that corresponds to the doctor ID from the storage section 402, and transmits the shake correction ID to the shake correction section 205. The observer mode that corresponds to the skill of the doctor is set in this manner, and the shake correction process that corresponds to the observer mode is performed.

The shake correction section 205 performs the shake correction process based on the shake correction ID. For example, the shake correction section 205 does not perform the shake correction process when the doctor is experienced, and performs the shake correction process when the doctor is inexperienced.

Note that the configuration is not limited thereto. For example, the shake correction section 205 may perform a strong shake correction process when the doctor is experienced. More specifically, the shake correction section 205 may detect the motion amount using the captured image in the current frame and the captured image in the preceding frame, and perform the shake correction process. On the other hand, the shake correction section 205 may perform a weak shake correction process when the doctor is inexperienced. More specifically, the shake correction section 205 may detect a plurality of motion amount, between frames using the captured image in the current frame and the captured images in a plurality of preceding frames, calculate the amount of a shake used for the shake correction process based on the motion amount obtained by integrating the plurality of motion amounts (see the following expression (4)), and perform the shake correction process.

$$BlurX = moveX - moveXav,$$

$$BlurY = moveY - moveYav,$$

$$moveXav' = (moveXav + moveX)/2,$$

$$moveYav' = (moveYav + moveY)/2 \quad (4)$$

where, BlurX is the amount of a shake of the captured image in the current frame that corresponds to the horizontal axis, and BlurY is the amount of a shake of the captured image in the current frame that corresponds to the vertical axis. moveX is the global motion amount of the captured image in the current frame that corresponds to the horizontal axis, and moveY is the global motion amount of the captured image in the current frame that corresponds to the vertical axis. moveXav is the integrated average global motion amount of the captured images in the preceding frames that corresponds to the horizontal axis, and moveYav is the integrated average global motion amount of the captured images in the preceding frames that corresponds to the vertical axis. moveXav' is the integrated average global motion amount of the captured image in the current frame that corresponds to the horizontal axis, and moveYav' is the integrated average global motion amount of the captured image in the current frame that corresponds to the vertical axis.

Specifically, the average motion amount within a given period (given frames) is calculated by averaging the motion amounts that are random with respect to time, the amount of a shake is calculated using the average motion amount, and the shake correction process is then performed. In this case, a delay in display image increases as the averaging period increases when the scope has been rapidly moved in a constant direction during screening observation. However, it is possible to improve the random shake correction accuracy during close observation. Note that the above method may be applied only when performing close observation.

According to the second embodiment, the shake correction process can be adaptively performed corresponding to the doctor's medical examination experience. This makes it possible to provide an optimum medical examination environment to each doctor.

2.2. Modification

Although an example in which the shake correction process is selected corresponding to the doctor's medical examination experience has been described above, the configuration is not limited thereto. For example, the shake correction method may be selected corresponding to the observation mode. Such a modification is described below.

Figure 13:
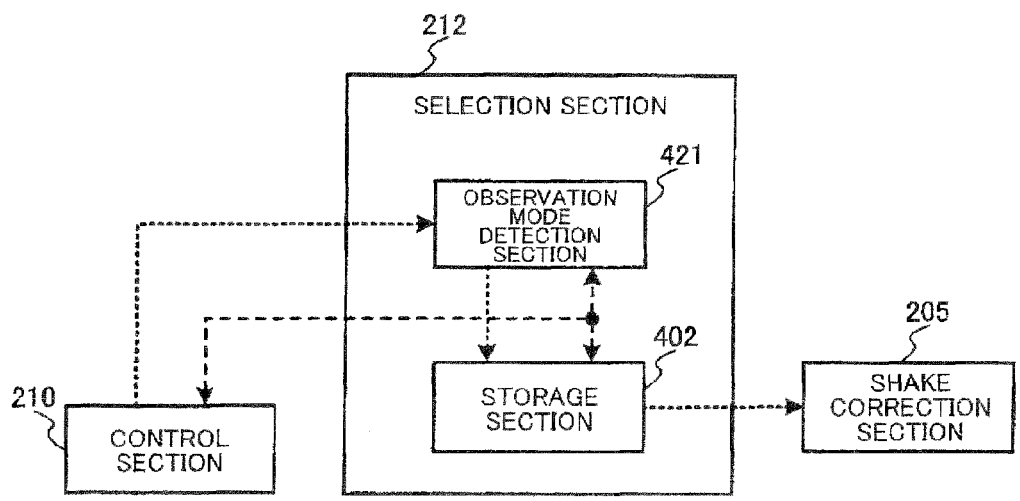
FIG. 13 illustrates a third specific configuration example of a selection section.

FIG. 13 illustrates a third specific configuration example of the selection section. As illustrated in FIG. 13, the selection section 212 includes an observation mode detection section 421 and the storage section 402. The observation mode detection section 421 is connected to the shake correction section 205 via the storage section 402. The control section 210 is bidirectionally connected to the observation mode detection section 421 and the storage section 402.

According to the modification, the shake correction process is performed corresponding to the observation mode (e.g., close observation or screening observation). More specifically, the shake correction ID that corresponds to an observation mode ID is stored in the storage section 402 in advance. The observation mode ID corresponds to each observation mode. For example, the doctor sets the observation mode ID via the external I/F section 211 when performing a medical examination. The observation mode detection section 421 reads the shake correction ID that corresponds to the observation mode ID from the storage section 402, and transmits the shake correction ID to the shake correction section 205 under control of the control section 210.

The shake correction section 205 performs the shake correction process based on the shake correction ID selected by the selection section 212. More specifically, the shake correction section 205 changes the level of the shake correction process corresponding to the shake correction ID. When the observation mode is the close observation mode, it is necessary to determine whether or not to perform a biopsy on a lesion area. Therefore, the amount of a shake is reduced by increasing the level of the shake correction process so that diagnosis can be performed accurately and quickly. When the observation mode is the screening mode, the motion amount detection accuracy may decrease since the scope is moved (operated) quickly. In this case, diagnosis may be hindered due to incorrect shake correction. Therefore, the shake correction process is performed in a state in which the level of the shake correction process is reduced.

For example, the number of frames used for detecting the motion amount is increased as the level of the shake correction process increases. When the observation mode is the screening mode, the motion amount is not detected, and the shake correction process is not performed, for example. When the observation mode is the close observation mode, the number of frames used to calculate the integrated average global motion amount (see the expression (4)) is set corresponding to the level of the shake correction process.

An appropriate shake correction process can be performed corresponding to the observation state by thus adaptively performing the shake correction process corresponding to the observation mode, so that diagnosis can be performed with high accuracy.

Although an example in which the shake correction ID is set corresponding to the observer mode or the observation mode has been described above, the configuration is not limited thereto. For example, the doctor may manually select the desired shake correction ID via the external I/F section 211 when performing a medical examination. For example, when the level of the shake correction process can be changed, and the doctor has determined that it is necessary to perform a medical examination while suppressing the motion amount as much as possible, the doctor may select the shake correction ID that corresponds to a high-level shake correction process via the external I/F section 211. When the doctor performs a quick operation, the doctor may select the shake correction ID that corresponds to a low-level shake correction process via the external I/F section 211 in order to prevent a situation in which the motion amount detection accuracy decreases.

According to the second embodiment, the endoscope apparatus includes the observation mode setting section (e.g., an observation mode setting section included in the control section 210 illustrated in FIG. 11) that sets the observation mode (observation mode I)) when observing the object. The selection section 212 includes the observation mode detection section 421 that detects the observation mode set by the observation mode setting section, and the storage section 402 that stores a plurality of pieces of shake correction parameter information (i.e., a plurality of shake correction ID) that respectively correspond to a plurality of observation modes (see FIG. 13). The selection section 212 selects the shake correction parameter information (shake correction ID) that corresponds to the observation mode detected by the observation mode detection section 421 from the plurality of pieces of shake correction parameter information stored in the storage section 402.

More specifically, the storage section 402 may store the shake correction parameter information that indicates the level of the shake correction process (e.g., the number of frames used to calculate the motion amount). The selection section 212 may select the shake correction parameter information that corresponds to a first level (first number of frames) when the observation mode detected by the observation mode detection section 421 is the screening mode, and may select the shake correction parameter information that corresponds to a second level (second number of frames) that is higher than the first level when the observation mode detected by the observation mode detection section 421 is the close observation mode.

The storage section 402 may store the shake correction parameter information that indicates whether or not to perform the shake correction process. In this case, the selection section 212 may select the shake correction parameter information that instructs not to perform the shake correction process when the observation mode detected by the observation mode detection section 421 is the screening mode, and may select the shake correction parameter information that instructs to perform the shake correction process when the observation mode detected by the observation mode detection section 421 is the close observation mode.

This makes it possible to perform an appropriate shake correction process corresponding to the observation mode. Specifically, it is possible to search for a lesion area in the screening mode while minimizing the effects of a display delay and the like by reducing the level of the shake correction process. On the other hand, it is possible to closely observe a lesion area in the close observation mode while suppressing a shake due to a random motion of the scope by increasing the level of the shake correction process.

Note that the observation mode may be set by the user via the external I/F section 211, or may be set corresponding to the magnifying power (magnification) of the lens system 201. For example, the observation mode may be set to the close observation mode during zoom observation in which the magnifying power is larger than a threshold value, and may be set to the screening mode during normal observation in which the magnifying power is smaller than a threshold value.

The endoscope apparatus may include the observer mode setting section (e.g., an observer mode setting section included in the control section 210 illustrated in FIG. 11) that sets the observer mode (doctor ID) that corresponds to the observer who operates the endoscope apparatus. The selection section 212 may include the observer mode detection section 411 that detects the observer mode set by the observer mode setting section, and the storage section 402 that stores a plurality of pieces of shake correction parameter information that respectively correspond to a plurality of observer modes (see FIG. 12). The selection section 212 may select the shake correction parameter information that corresponds to the observer mode detected by the observer mode detection section 411 from the plurality of pieces of shake correction parameter information stored in the storage section 402.

More specifically, the storage section 402 may store the parameter information that corresponds to the number of frames of the captured image used to detect the motion amount (i.e., the number of frames over which the integrated average global motion amount is calculated (see the expression (4))). The selection section 212 may select the shake correction parameter information that corresponds to a first number of frames when the observer mode detected by the observer mode detection section 411 is a first observer mode, and may select the shake correction parameter information that corresponds to a second number of frames that is larger than the first number of frames when the observer mode detected by the observer mode detection section 411 is a second observer mode.

The second observer mode may correspond to the observer having a skill higher than that of the observer who corresponds to the first observer mode.

The endoscope apparatus may include an input section (external I/F section 211 illustrated in FIG. 11) that allows the observer to input the observer mode. The selection section 212 may select the parameter information corresponding to the observer mode input by the observer.

This makes it possible to perform an appropriate shake correction process corresponding to the user who operates the endoscope apparatus. Specifically, when an experienced user operates the endoscope apparatus, a display delay and the like can be suppressed by reducing the number of frames used to calculate the motion amount. When an inexperienced user operates the endoscope apparatus, a shake due to a random motion of the scope can be suppressed by increasing the number of frames used to calculate the motion amount. This makes it possible to prevent a situation in which a lesion area is missed even if the user is inexperienced.

3. Third Embodiment 3.1. Configuration Example

A third embodiment of the invention is described below. In the third embodiment, the shake correction process is performed corresponding to normal observation or zoom observation.

Figure 14:
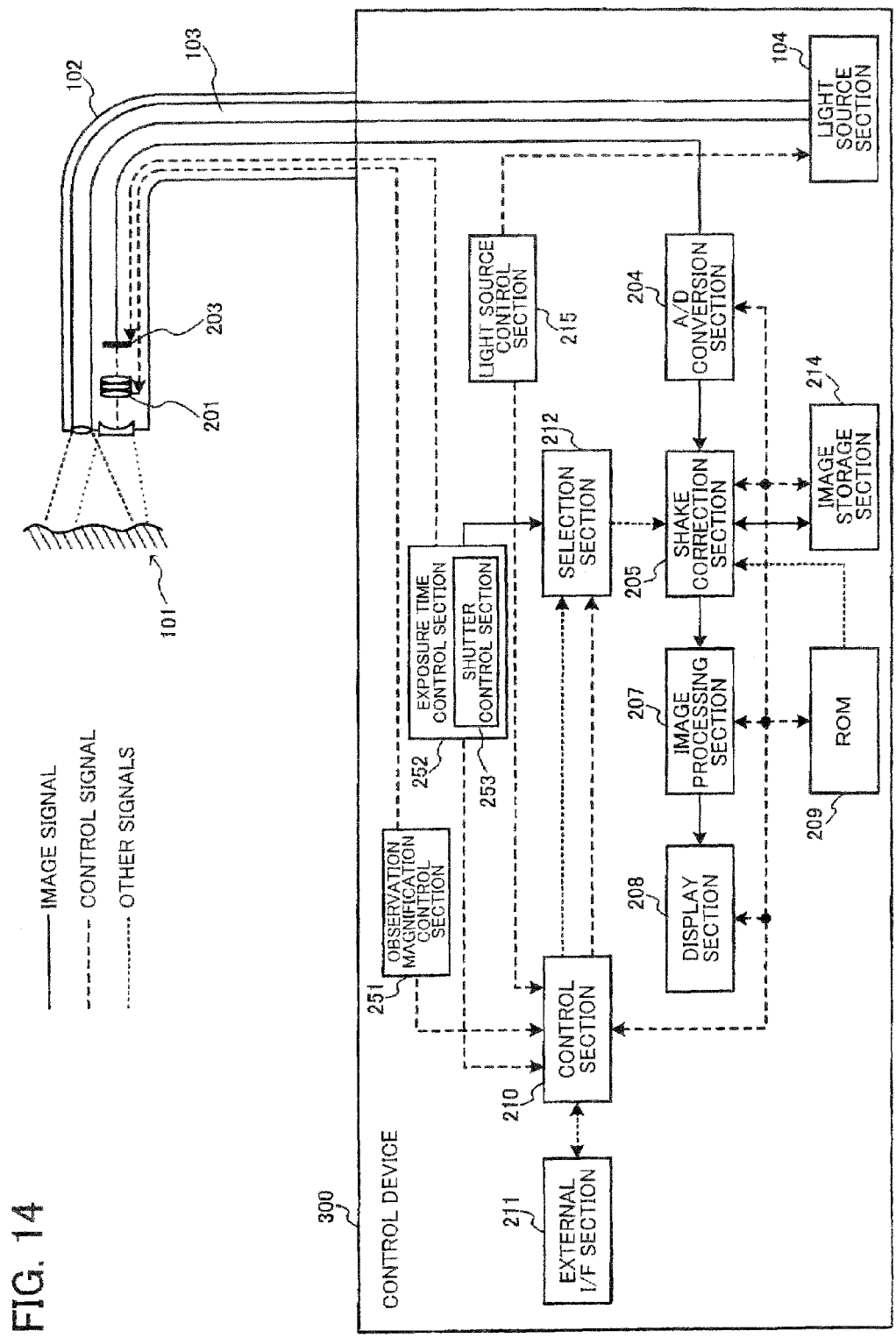
FIG. 14 illustrates a third configuration example of an endoscope apparatus.

FIG. 14 illustrates a third configuration example of the endoscope apparatus. As illustrated in FIG. 14, the endoscope apparatus includes a control device 300 and an imaging section 102. The imaging section 102 includes a light guide 103, a lens system 201, and an imaging element 203. The control device 300 includes a light source section 104, an A/D conversion section 204, a shake correction section 205, an image processing section 207, a display section 208, a ROM 209, a selection section 212, an image storage section 214, a light source control section 215, an observation magnification control section 251 (lens control section in a broad sense), an exposure time control section 252 (imaging element control section in a broad sense), a control section 210, and an external I/F section 211.

The third embodiment differs from the first embodiment in that the observation magnification control section 251 and the exposure time control section 252 are provided instead of the lens control section 216 and the imaging element control section 217, and the selection section 212 operates in a different way. The following description focuses on the differences from the first embodiment, and description of the same elements as those described in connection with the first embodiment is appropriately omitted.

The endoscope apparatus according to the third embodiment is configured so that the object is observed while changing the observation mode (state) between normal observation and zoom observation (i.e., changing the observation magnification of the observation optical system). When the doctor has found a lesion area during a medical examination, the doctor moves the end of the imaging section closer to the lesion area, and increases the observation magnification to perform zoom observation. When the doctor has determined that the lesion area is malignant, the doctor performs a treatment by endoscopic submucosal dissection (ESD) or the like. When the doctor cannot determine whether or not the lesion area is malignant, the doctor collects a sample of the lesion area, performs a pathological examination on the sample, and determines a treatment strategy.

The observation magnification control section 251 adjusts the observation magnification by controlling the lens system 201 to switch the observation mode between normal observation and zoom observation. The doctor sets the observation magnification via the external I/F section 211. The observation mode is determined to be zoom observation when the observation magnification set by the doctor is larger than a given observation magnification threshold value, and is determined to be normal observation when the observation magnification set by the doctor is smaller than the given observation magnification threshold value.

A lesion area can be accurately diagnosed by zoom observation as compared with normal observation. However, the display image appears to be blurred to a large extent during zoom observation as compared with normal observation due to peristalsis in the internal organ, the operation performed by the doctor, and the like. The display image (captured image) is blurred to a larger extent as the magnification increases. In this case, it is likely that the amount of a shake is not sufficiently reduced when the shake correction process is similarly performed during normal observation and zoom observation. On the other hand, a delay in display of the captured image may occur when increasing the level of the shake correction process.

In the third embodiment, the shake correction section 205 corrects a shake that occurs between frames, and suppresses a blur (e.g., image blur) within each frame by increasing the shutter speed. The intensity of light emitted from the light source is increased by performing an intensity adjustment process (e.g., known intensity adjustment process) to maintain the brightness of the captured image.

More specifically, when the doctor desires to perform zoom observation, the doctor moves the end of the imaging section closer to the lesion area, and sets the observation magnification via the external I/F section 211. The lens system 201 is adjusted to implement zoom observation under control of the observation magnification control section 251.

As illustrated in FIG. 13, the selection section 212 includes the observation mode detection section 421 and the storage section 402. Information about an observation ID that corresponds to normal observation and an observation ID that corresponds to zoom observation is input to the observation mode detection section 421 from the control section 210. The observation mode detection section 421 reads an exposure control ID that corresponds to the observation ID from the storage section 402, and outputs the exposure control ID to the exposure time control section 252 and the light source control section 215.

Figure 15:
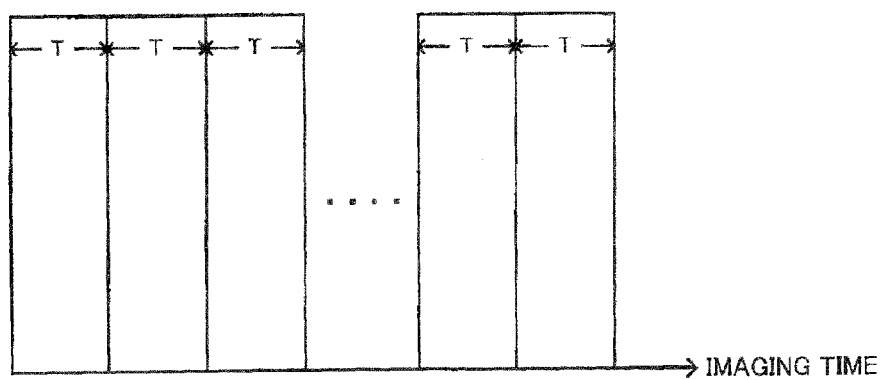
FIG. 15 is a view illustrating an exposure time control process.
Figure 16:
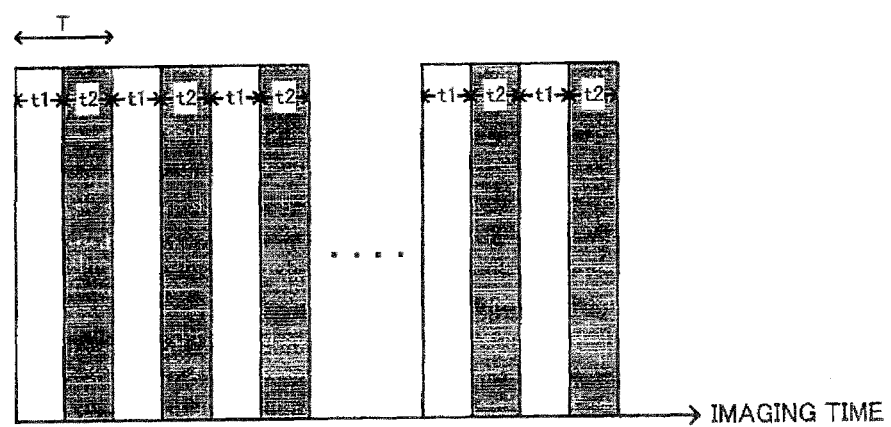
FIG. 16 is a view illustrating an exposure time control process.

The exposure time control section 252 controls the exposure time during the imaging operation based on the exposure control ID transmitted from the selection section 212. More specifically, the exposure time control section 252 includes a shutter control section 253. The shutter control section 253 adjusts the exposure time by controlling the electronic shutter of the imaging element 203. As illustrated in FIG. 15, the object 101 is captured in time series during normal observation using a given period T (time) as the exposure time, for example. As illustrated in FIG. 16, the shutter control section 253 controls the electronic shutter of the imaging element 203 during zoom observation, and the object 101 is captured using a given period t1 within the period T as the exposure time. The object 101 is not captured within a given period t2 subsequent to the period t1. The relationship between the periods t1, t2, and T is shown by the following expression (5). The information about the periods t1, t2, and T may be stored in the ROM 212 in advance, or the doctor may input the information about the periods t1, t2, and T via the external I/F section 211. Note that the imaging period (exposure time) is returned to the period T when the observation mode is switched from zoom observation to normal observation.

$$T=t1+t2 \qquad (5)$$

Figure 17:
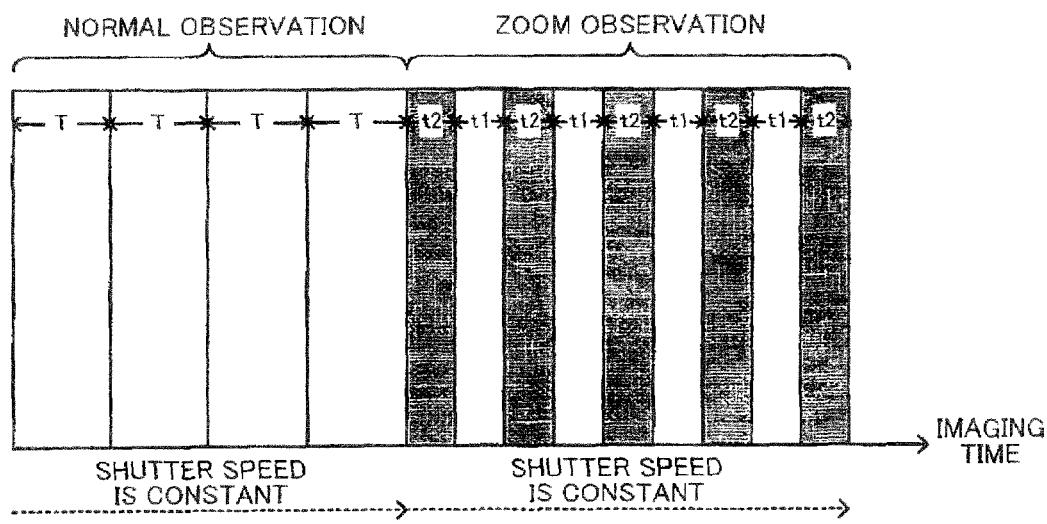
FIG. 17 is a view illustrating an exposure time control process.
Figure 18:
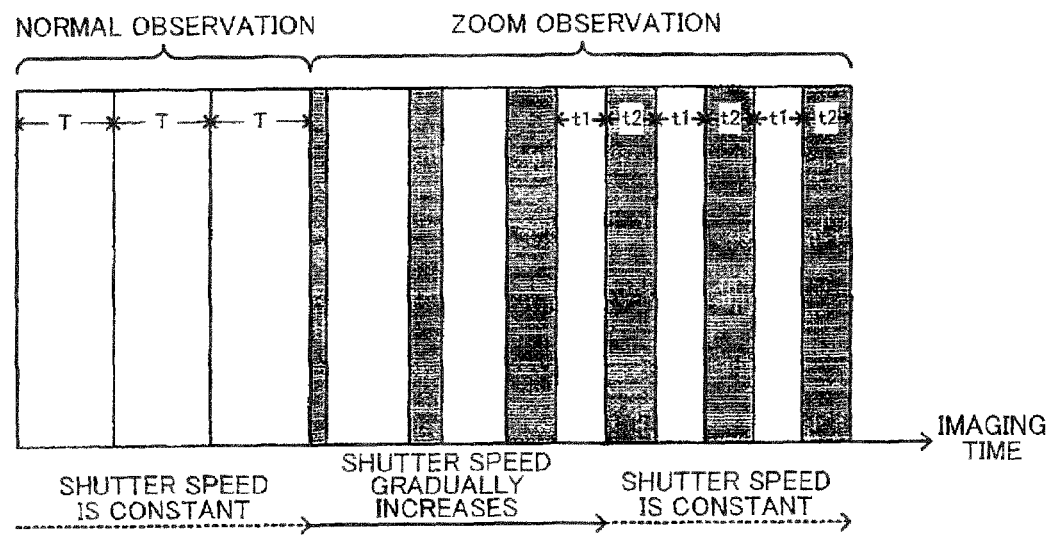
FIG. 18 is a view illustrating an exposure time control process.

When the observation mode is switched from normal observation to zoom observation, the imaging period may be instantaneously changed from the period T to the period t1 (see FIG. 17), or may be gradually reduced from the period T to the period t1 (see FIG. 18). When the observation mode is switched from zoom observation to normal observation, the imaging period may be instantaneously changed from the period t1 to the period T, or may be gradually increased from the period t1 to the period T.

According to the above configuration, since the exposure time is reduced during zoom observation as compared with normal observation by controlling the electronic shutter, a blur of the captured image within each frame can be suppressed. However, the brightness of the captured image acquired during zoom observation decreases as compared with the brightness of the captured image acquired during normal observation due to a decrease in exposure time. In order to deal with this problem, the intensity of light emitted from the light source is controlled by performing an intensity adjustment process that corresponds to the exposure control ID.

Figure 19:
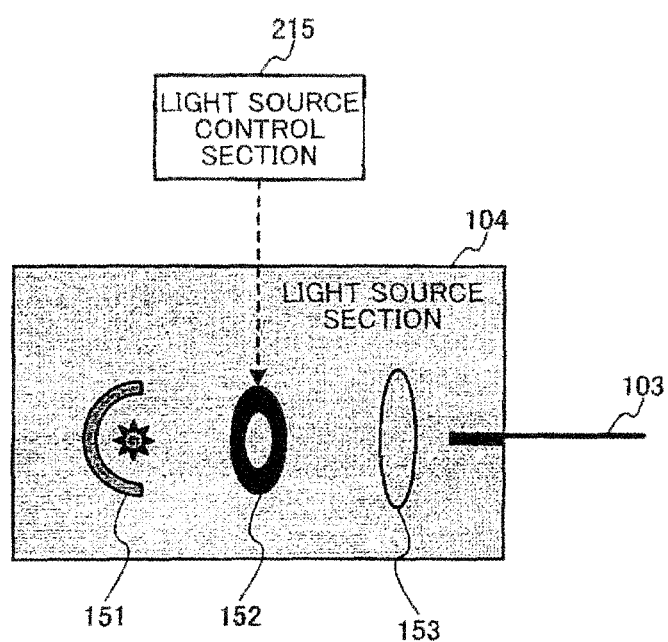
FIG. 19 illustrates a specific configuration example of a light source section.

FIG. 19 illustrates a specific configuration example of the light source section. As illustrated in FIG. 19, the light source section 104 includes a light source 151, a light source aperture 152, and an illumination optical system 153.

Light emitted from the light source 151 enters the light guide 103 via the light source aperture 152 and the illumination optical system 153. The intensity adjustment process includes adjusting the light source aperture 152 to have an open area corresponding to the shutter speed under control of the light source control section 215 when the observation mode has been switched from normal observation to zoom observation. The brightness of the captured image can be maintained (almost) constant by thus adjusting the light source aperture 152 corresponding to the shutter speed.

A blur of the captured image within each frame can be suppressed during zoom observation by thus increasing the shutter speed to reduce the exposure time while performing the shake correction process using image processing. The accuracy of matching between frames can be improved by suppressing a blur (image blur) within each frame, so that the electronic shake correction accuracy can be improved.

Note that an LED light source may be used as the light source. In this case, the intensity of light emitted from the light source can be increased by increasing the amount of current that flows through the light source by increasing the voltage applied to the light source while increasing the shutter speed.

Although an example in which the doctor selects the observation mode ID that corresponds to normal observation or zoom observation via the external I/F section and the information about the observation mode ID is transmitted to the selection section 212 has been described above, another configuration may also be employed. For example, when the doctor moves the end of an endoscope apparatus having an autofocus function closer to the object, and observes the object, the position of the lens system 201 may be automatically adjusted so that the object is in focus under control of the observation magnification control section 251. In this case, the selection section 212 may acquire information about the in-focus object plane, and determine the observation state from the in-focus object plane under control of the control section 210. For example, the selection section 212 may compare the in-focus object plane with a given threshold value, and determine that the observation state is zoom observation when the in-focus object plane is smaller than the threshold value (e.g. the end of the endoscope apparatus is positioned close to the object). The selection section 212 may determine that the observation state is normal observation when the in-focus object plane is larger than the threshold value (e.g., the end of the endoscope apparatus is positioned away from the object). When the endoscope apparatus has an autofocus function, the distance between the end of the imaging section and the object can be calculated based on information about the in-focus focal distance. Therefore, the shutter speed may be gradually increased as the distance between the end of the imaging section and the object decreases, and the brightness of the captured image may be controlled to be constant by adjusting the intensity of illumination light.

3.2. Modification

Although an example in which a blur is suppressed by adjusting the shutter speed has been described above, another configuration may also be employed. For example, a blur may be suppressed by adjusting the frame rate. Such a modification is described below.

Figure 20:
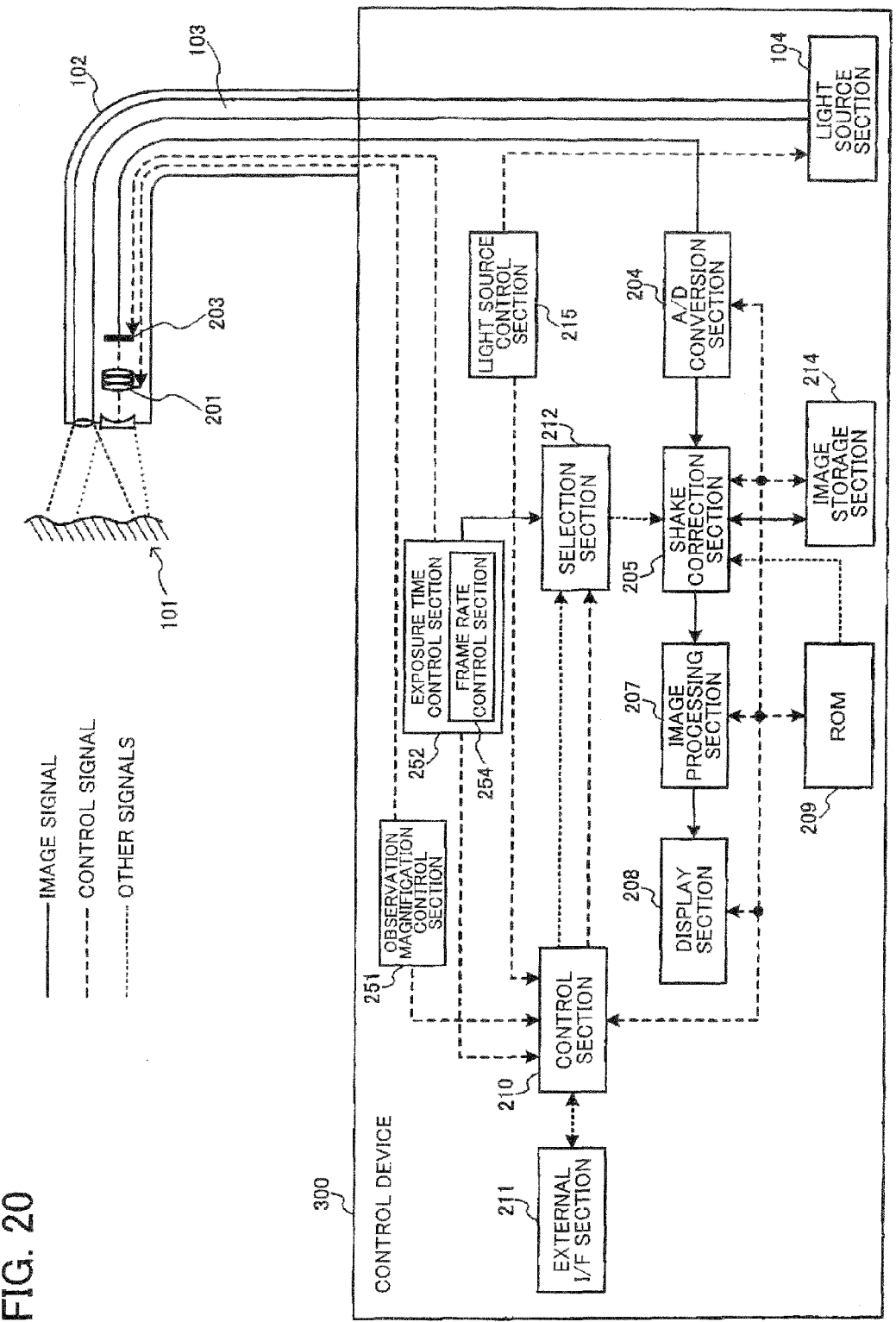
FIG. 20 illustrates a modified configuration example of an endoscope apparatus.

FIG. 20 illustrates a modified configuration example of the endoscope apparatus. As illustrated in FIG. 20, the endoscope apparatus includes a control device 300 and an imaging section 102. The imaging section 102 includes a light guide 103, a lens system 201, and an imaging element 203. The control device 300 includes a light source section 104, an A/D conversion section 204, a shake correction section 205, an image processing section 207, a display section 208, a ROM 209, a selection section 212, an image storage section 214, a light source control section 215, an observation magnification control section 251 (lens control section in a broad sense), an exposure time control section 252 (imaging element control section in a broad sense), a control section 210, and an external I/F section 211.

The configuration according to the modification is the same as the configuration described in connection with the third embodiment, except that the exposure time control section 252 includes a frame rate control section 254 instead of the shutter control section 253. The following description focuses on the differences from the third embodiment, and description of the same elements as those described in connection with the third embodiment is appropriately omitted.

In the modification, the shake correction section 205 corrects a shake that occurs between frames, and suppresses a blur (image blur) within each frame by adjusting the frame rate during the imaging operation. The intensity of light emitted from the light source is increased after performing an intensity adjustment process (e.g., known intensity adjustment process) to maintain the brightness of the captured image.

More specifically, when the doctor performs zoom observation, the doctor moves the end of the imaging section closer to the lesion area, and sets the observation magnification via the external I/F section 211. The lens system 201 is adjusted to implement zoom observation under control of the observation magnification control section 251.

As illustrated in FIG. 13, the selection section 212 includes the observation mode detection section 421 and the storage section 402. Information about the observation ID that corresponds to normal observation and the observation ID that corresponds to zoom observation is input to the observation mode detection section 421 from the control section 210. The observation mode detection section 421 reads the exposure control ID that corresponds to the observation ID from the storage section 402, and outputs the exposure control ID to the exposure time control section 252 and the light source control section 215.

The exposure time control section 252 includes the frame rate control section 254 that controls the frame rate of the imaging element 203 based on the exposure control ID. The frame rate control section 254 increases the frame rate during zoom observation as compared with the frame rate during normal observation. For example, the frame rate control section 254 controls the frame rate so that an image is captured at a frame rate of 30 fps during normal observation, and is captured at a frame rate of 60 fps during zoom observation.

According to the above configuration, since the time in which an image corresponding to one frame is captured is reduced during zoom observation, the amount of blur (image blur) within each frame can be reduced. Since the motion amount of the object between frames decreases due to a decrease in interval between frames, the electronic shake correction accuracy can be improved. Moreover, a display delay due to the electronic shake correction process can be suppressed due to a decrease in interval between frames.

According to the third embodiment, the endoscope apparatus may include the exposure time control section 252 that controls the exposure time when capturing the captured image (see FIG. 14). The exposure time control section 252 may adjust the exposure time based on the shake correction parameter information (exposure control ID) selected by the selection section 212.

More specifically, the selection section 212 may select the shake correction parameter information that corresponds to a first exposure time (i.e., the period T in FIG. 15) during normal observation, and may select the shake correction parameter information that corresponds to a second exposure time (i.e. the period t1 in FIG. 16, t1<T) that is shorter than the first exposure time during zoom observation.

As illustrated in FIG. 14, the exposure time control section 252 may include the shutter control section 253 that controls the shutter speed (i.e., the exposure time using the electronic shutter of the imaging element 203) when capturing the captured image. The exposure time control section 252 may adjust the exposure time by controlling the shutter speed.

As illustrated in FIG. 20, the exposure time control section 252 may include the frame rate control section 254 that controls the frame rate when capturing the captured image. In this case, the exposure time control section 252 may adjust the exposure time by controlling the frame rate.

According to the above configuration, since the exposure time can be reduced during zoom observation in which the amount of a shake increases due to an increase in magnification of the optical system, a blur (image blur) within each frame can be suppressed. This makes it possible to improve the accuracy of matching between frames during the shake correction process.

The endoscope apparatus may include the observation magnification control section 251 that controls the observation magnification of the imaging section 102, and the selection section 212 may include the storage section 402 that stores the plurality of pieces of shake correction parameter information (i.e. a plurality of shake correction ID) that correspond to the observation magnification (see FIG. 14). In this case, the selection section 212 may select the shake correction parameter information (shake correction ID) from the plurality of pieces of shake correction parameter information stored in the storage section 402 corresponding to the observation magnification.

More specifically, the storage section 402 may store the shake correction parameter information that indicates the level of the shake correction process (e.g. the number of frames used to calculate the motion amount). The selection section 212 may select the shake correction parameter information that corresponds to a first level (i.e., a first number of frames) during normal observation in which the observation magnification is smaller than a threshold value, and may select the shake correction parameter information that corresponds to a second level that is higher than the first level (i.e. a second number of frames that is larger than the first number of frames) during zoom observation in which the observation magnification is larger than the threshold value.

This makes it possible to perform an appropriate shake correction process corresponding to the observation magnification. Specifically, it is possible to suppress a blur and improve the visibility of the object by increasing the level of the shake correction process during zoom observation in which the amount of a shake increases due to an increase in magnification of the optical system.

4. Fourth Embodiment

A fourth embodiment of the invention is described below. In the fourth embodiment, a white light source and a special light source are selectively used, and the shake correction process is performed corresponding to the light source.

Figure 21:
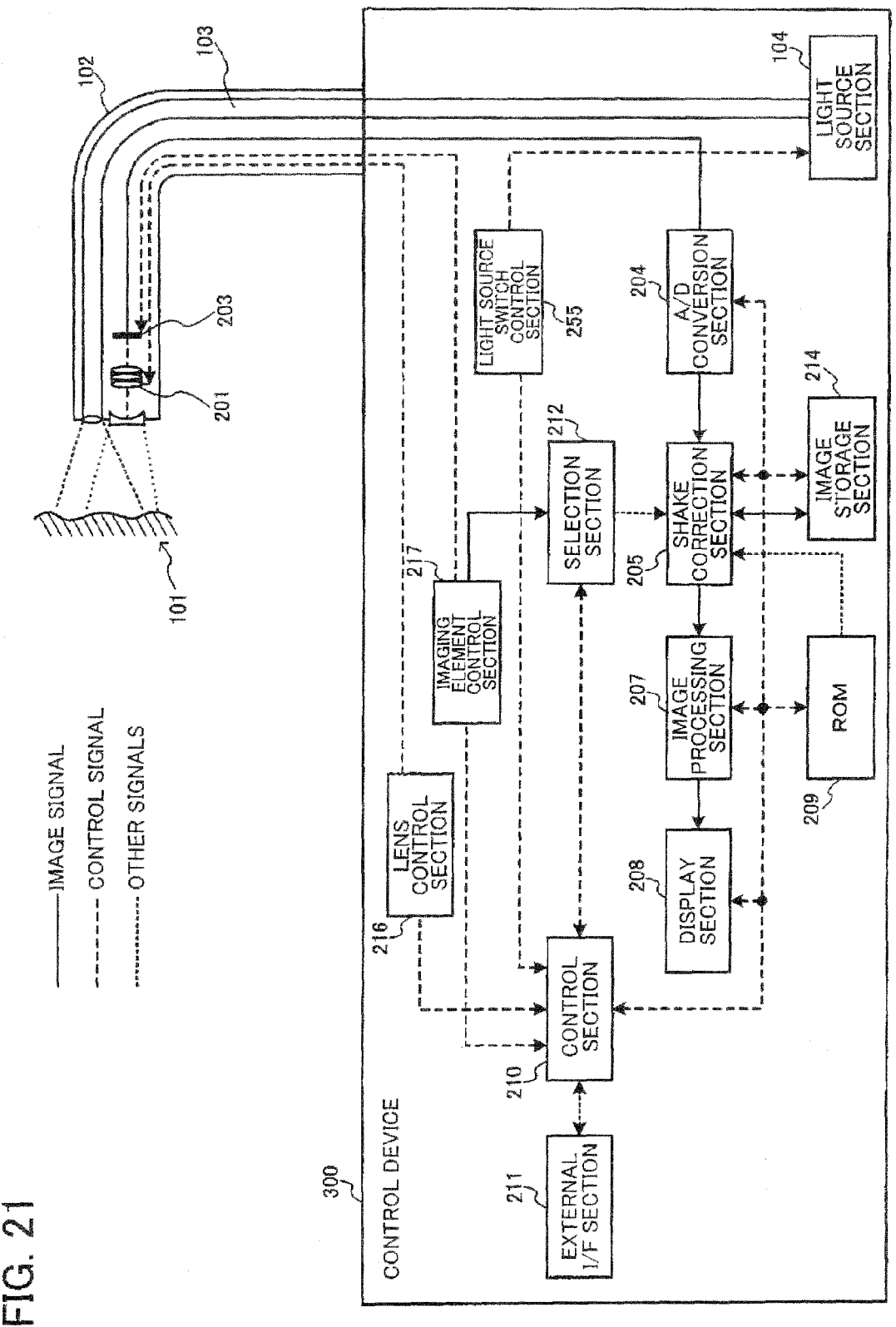
FIG. 21 illustrates a fourth configuration example of an endoscope apparatus.

FIG. 21 illustrates a fourth configuration example of the endoscope apparatus. As illustrated in FIG. 21, the endoscope apparatus includes a control device 300 and an imaging section 102. The imaging section 102 includes a light guide 103, a lens system 201, and an imaging element 203. The control device 300 includes a light source section 104, an A/D conversion section 204, a shake correction section 205, an image processing section 207, a display section 208, a ROM 209, a selection section 212, an image storage section 214, a light source switch control section 255 (light source control section in a broad sense), a lens control section 216, an imaging element control section 217, a control section 210, and an external I/F section 211.

The configuration of the endoscope apparatus according to the fourth embodiment is the same as the configuration of the endoscope apparatus according to the first embodiment, except that the light source switch control section 255 is provided instead of the light source control section 215, and the selection section 212 operates in a different way. The following description focuses on the differences from the first embodiment, and description of the same elements as those described in connection with the first embodiment is appropriately omitted.

Figure 22:
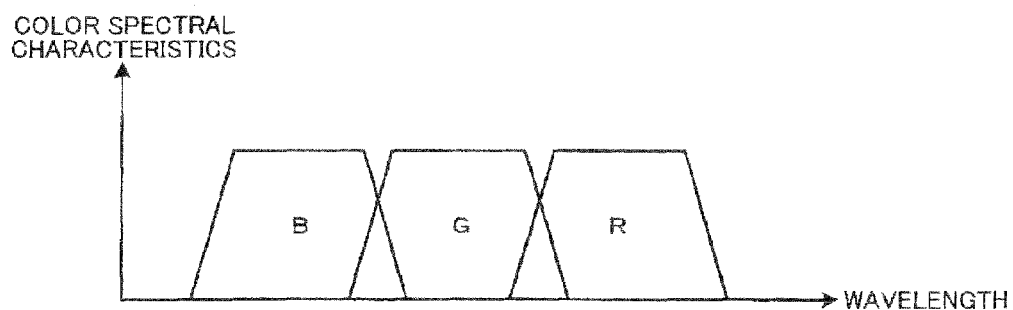
FIG. 22 illustrates the spectral characteristics of white light.

The light source section 104 according to the first to third embodiments utilizes a white light source. As illustrated in FIG. 22, white light emitted from the white light source has spectral characteristics indicated R (580 to 700 nm), G (480 to 600 nm), and B (400 to 500 nm). A normal light image is obtained by applying white light to the object 101, and capturing reflected (return) light from the object 101.

Figure 23:
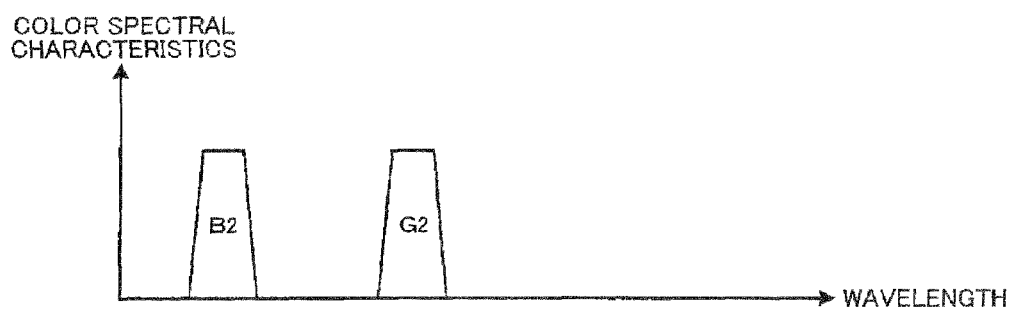
FIG. 23 illustrates the spectral characteristics of special light.

The endoscope apparatus according to the fourth embodiment is configured so that a white light source and a special light source can be selectively used. An example in which the special light source is an NBI light source, the special light is narrow-band light, and the special light image is an NBI image is described below. Note that the configuration is not limited thereto. As illustrated in FIG. 23, narrow-band light emitted from the NBI light source has narrow-band spectral characteristics indicated by G2 (530 to 550 nm) and B2 (390 to 445 nm). The narrow-band light is easily absorbed by hemoglobin in blood. In the field of endoscopic diagnosis, the narrow-band light is applied to tissue to acquire an NBI image in which capillaries and a fine mucosal pattern in a surface layer of a mucous membrane are enhanced. The NBI image is effective for diagnosis of esophagus cancer, large bowel cancer, gastric cancer, and the like.

Since the NBI light source has narrow spectral band characteristics, an image captured using the NBI light source is darker than an image captured using a white light source even if the brightness of the captured image is controlled using an intensity adjustment process. The intensity adjustment process may apply an analog gain or a digital gain to the captured image in order to compensate for insufficient brightness. In this case, however, the amount of noise of the captured image is amplified.

Figure 24:
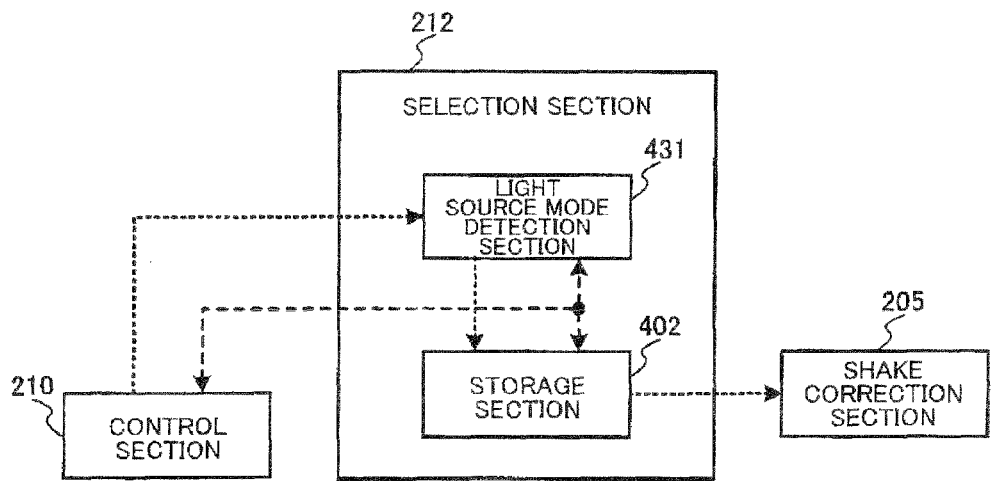
FIG. 24 illustrates a fourth specific configuration example of a selection section.

According to the fourth embodiment, the level of the shake correction process is adjusted corresponding to the light source. FIG. 24 illustrates a fourth specific configuration example of the selection section. As illustrated in FIG. 24, the selection section 212 includes a light source mode detection section 431 and a storage section 402.

The doctor sets the light source mode (observation mode in a broad sense) that corresponds to the white light source or the NBI light source via the external I/F section 211. The light source of the light source section 104 is switched to the light source that corresponds to the light source mode under control of the light source switch control section 255. A light source mode ID (observation mode ID in a broad sense) that corresponds to the light source mode is input to the light source mode detection section 431 from the control section 210. The observation mode detection section 421 reads the shake correction ID that corresponds to the light source mode ID from the storage section 402, and transmits the shake correction ID to the shake correction section 205 under control of the control section 210.

The shake correction section 205 performs the shake correction process that corresponds to the shake correction ID transmitted from the selection section 212 under control of the control section 210. When performing a medical examination using the NBI light source, the amount of noise of an image captured using the NBI light source is amplified due to analog/digital gain control during the intensity adjustment process. Therefore, the motion amount detection accuracy may decrease as compared with an image captured using the white light source due to the effects of noise. The image obtained by the shake correction process may be corrupted due to a decrease in detection accuracy. According, to the fourth embodiment, the level of the shake correction process employed when capturing an image using the NBI light source is reduced as compared with the level of the shake correction process employed when capturing an image using the white light source. More specifically, when the light source mode ID that corresponds to the NBI light source has been set, the shake correction ID is selected so that the level of the shake correction process is lower than that when the light source mode ID that corresponds to the white light source is selected.

For example, the number of frames used for detecting the motion amount is increased as the level of the shake correction process decreases. For example, when the light source mode ID that corresponds to the white light source has been set, the motion amount is calculated from the captured image in the current frame and the captured image in the preceding frame, and the shake correction process is performed using the calculated motion amount. When the light source mode ID that corresponds to the special light source has been set, the motion amount is calculated from the captured image in the current frame and the captured images in a plurality of preceding frames, and the shake correction process is performed using the calculated motion amount.

Note that the level of the shake correction process may be set corresponding to the number of light guides, the thickness of each light guide, or the like. Specifically, the brightness of the captured image may differ depending on the number of light guides, the thickness of each light guide, or the like even when using the white light source. A relatively bright captured image is normally obtained when the number of light guides is large and each light guide has a large thickness. On the other hand, a relatively dark captured image is obtained when the number of light guides is small and each light guide has a small thickness. When the captured image is dark, the amount of noise of the captured image is amplified. This problem may be solved by setting the shake correction ID that corresponds to a high-level shake correction process when the number of light guides is large and each light guide has a large thickness, and setting the shake correction ID that corresponds to a low-level shake correction process when the number of light guides is small and each light guide has a small thickness.

The shake correction effect can be reliably obtained by thus controlling the level of the shake correction process corresponding to each light source when performing a medical examination while selectively using the special light source or the white light source. It is also possible to prevent a situation in which the image is corrupted when the motion amount cannot be accurately detected due to amplification of noise.

According to the fourth embodiment, the endoscope apparatus includes the light source switch control section 255 see FIG. 21). The light source switch control section 255 switches the light source between the white light source that emits white light and the special light source that emits special light, the special light being light within a specific wavelength band. The selection section 212 may include the light source mode detection section 431 that detects the light source that emits light applied to the object, and the storage section 402 that stores a plurality of pieces of shake correction parameter information (i.e., a plurality of light source mode ID) that respectively correspond to a plurality of light sources (see FIG. 24). The selection section 212 selects the shake correction parameter information (light source mode ID) from the plurality of pieces of shake correction parameter information stored in the storage section 402 corresponding to the light source detected by the light source mode detection section.

More specifically, the storage section 402 may store the shake correction parameter information that indicates the level of the shake correction process (e.g. the number of frames used to calculate the motion amount). The selection section 212 may select the shake correction parameter information that corresponds to a first level (first number of frames) when the captured image has been acquired by applying white light, and may select the shake correction parameter information that corresponds to a second level lower than the first level (i.e. a second number of frames larger than the first number of frames) when the captured image has been acquired by applying special light.

This makes it possible to perform an appropriate shake correction process corresponding to the light source. Specifically, it is possible to suppress a decrease in matching accuracy due to an increase in noise by reducing the level of the shake correction process when capturing an image using the special light.

The specific wavelength band may be narrower than the wavelength band (e.g. 380 to 650 nm) of white light (i.e., narrow band imaging (NBI)). For example, the white light image (normal light image) and the special light image may be an in vivo image, and the specific wavelength band included in the in vivo image may be the wavelength band of light absorbed by hemoglobin in blood. The wavelength band of light absorbed by hemoglobin may be 390 to 445 nm (first narrow-band light or a B2 component of narrow-band light) or 530 to 550 nm (second narrow-band light or a G2 component of narrow-band light), for example.

This makes it possible to observe the structure of a blood vessel positioned in a surface area and a deep area of tissue. A lesion area (e.g., epidermoid cancer) that is difficult to observe using normal light can be displayed in brown or the like by inputting the resulting signal to a given channel (G2→R, B2→G, and B), so that the lesion area can be reliably detected. A wavelength band of 390 to 445 nm or a wavelength band of 530 to 550 nm is selected from the viewpoint of absorption by hemoglobin and the ability to reach a surface area or a deep area of in vivo tissue. Note that the wavelength band is not limited thereto. For example, the lower limit of the wavelength band may decrease by about 0 to 10%, and the upper limit of the wavelength band may increase by about 0 to 10%, depending on a variation factor (e.g., experimental results for absorption by hemoglobin and the ability to reach a surface area or a deep area of in vivo tissue).

The white light image and the special light image may be an in vivo image, and the specific wavelength band included in the in vivo image may be the wavelength band of fluorescence produced by a fluorescent substance. For example, the specific wavelength band may be 490 to 625 nm.

This makes it possible to implement autofluorescence imaging (AFI). Intrinsic fluorescence (490 to 625 nm) produced by a fluorescent substance (e.g., collagen) can be observed by applying excitation light (390 to 470 nm). In this case, since a lesion can be highlighted in a color differing from that of a normal mucous membrane, a lesion area can be reliably detected, for example. The wavelength band of 490 to 625 nm is the wavelength band of intrinsic fluorescence produced by a fluorescent substance (e.g. collagen) when excitation light is applied. Note that the wavelength band is not limited thereto. For example, the lower limit of the wavelength band may decrease by about 0 to 10%, and the upper limit of the wavelength band may increase by about 0 to 10% depending on a variation factor (e.g., experimental results for the wavelength band of fluorescence produced by a fluorescent substance). A pseudo-color image may be generated by simultaneously applying light within a wavelength band (540 to 560 nm) that is absorbed by hemoglobin.

Several embodiments of the invention and the modifications thereof have been described above. Note that the invention is not limited to the above embodiments and the modifications thereof. Various modifications and variations may be made without departing from the scope of the invention. A plurality of elements described in connection with the above embodiments and the modifications thereof may be appropriately combined to implement various configurations. For example, some of the elements described in connection with the above embodiments and the modifications thereof may be omitted. Some of the elements described in connection with different embodiments or modifications thereof may be appropriately combined. Specifically, various modifications and applications are possible without materially departing from the novel teachings and advantages of the invention.

Any term cited with a different term having a broader meaning or the same meaning at least once in the specification and the drawings can be replaced by the different term in any place in the specification and the drawings.

Although only some embodiments of the invention have been described in detail above, those skilled in the art would readily appreciate that many modifications are possible in the embodiments without materially departing from the novel teachings and advantages of the invention. Accordingly, such modifications are intended to be included within the scope of the invention.

What is claimed is:

1. An endoscope apparatus comprising:
    an imaging section that includes an imaging optical system and an imaging element, and captures images; and
    a processor that performs operations including:
    selecting shake correction parameter information from a plurality of pieces of shake correction parameter information based on an observation state of the imaging section;
    detecting a motion amount of an object between the captured images; and
    performing a shake correction process on the captured images based on the detected motion amount;
    wherein:
    the shake correction parameter information is selected to correspond to the observation state of the imaging section attached to the endoscope apparatus;
    the motion amount is detected using a detection method that corresponds to the selected shake correction parameter information;
    a plurality of types of the imaging section are removably attachable to the endoscope apparatus;
    selecting the shake correction parameter information comprises detecting a type of the imaging section attached to the endoscope apparatus, and selecting the shake correction parameter information from a storage device that stores the plurality of pieces of shake correction parameter information that respectively correspond to the plurality of types of the imaging section; and
    the processor performs operations further comprising:
        performing an edge enhancement process on the captured images,
        selecting the shake correction parameter information that corresponds to a first intensity of the edge enhancement process when the imaging element of the imaging section attached to the endoscope apparatus has a first size, and selecting the shake correction parameter information that corresponds to a second intensity of the edge enhancement process when the imaging element has a second size, the second intensity being higher than the first intensity, and the second size being smaller than the first size, and
        performing the edge enhancement process at an intensity that corresponds to the selected shake correction parameter information.

2. An endoscope apparatus comprising:
an imaging section that includes an imaging optical system and an imaging element, and captures images; and
a processor that performs operations including:
selecting shake correction parameter information from a plurality of pieces of shake correction parameter information based on an observation state of the imaging section;
detecting a motion amount of an object between the captured images; and
performing a shake correction process on the captured images based on the detected motion amount;
wherein:
the shake correction parameter information is selected to correspond to the observation state of the imaging section attached to the endoscope apparatus;
the motion amount is detected using a detection method that corresponds to the selected shake correction parameter information;
the processor performs operations further comprising:
setting an observer mode that corresponds to an observer who operates the endoscope apparatus,
detecting the set observer mode, and accessing a storage device that stores a plurality of pieces of shake correction parameter information that respectively correspond to a plurality of the observer modes, and
selecting the shake correction parameter information that corresponds to the detected observer mode from the plurality of pieces of shake correction parameter information stored in the storage device;
the storage device stores a plurality of pieces of shake correction parameter information about a number of frames of the captured images used to detect the motion amount, and
the shake correction parameter information is selected to correspond to a first number of frames when the detected observer mode is a first observer mode, and to correspond to a second number of frames that is larger than the first number of frames when the detected observer mode is a second observer mode.

3. The endoscope apparatus as defined in claim 2, wherein:
the second observer mode corresponds to an observer having a skill level higher than an observer who corresponds to the first observer mode.

4. An endoscope apparatus comprising:
an imaging section that includes an imaging optical system and an imaging element, and captures images; and
a processor that performs operations including:
selecting shake correction parameter information from a plurality of pieces of shake correction parameter information based on an observation state of the imaging section;
detecting a motion amount of an object between the captured images; and
performing a shake correction process on the captured images based on the detected motion amount;
wherein:
the shake correction parameter information is selected to correspond to the observation state of the imaging section attached to the endoscope apparatus;
the motion amount is detected using a detection method that corresponds to the selected shake correction parameter information; and
the processor performs operations further comprising:
controlling an exposure time when capturing the captured images,
adjusting the exposure time based on the selected shake correction parameter information,
controlling a frame rate when capturing the captured images, and
adjusting the exposure time by controlling the frame rate.

5. An endoscope apparatus comprising:
an imaging section that includes an imaging optical system and an imaging element, and captures images; and
a processor that performs operations including:
selecting shake correction parameter information from a plurality of pieces of shake correction parameter information based on an observation state of the imaging section;
detecting a motion amount of an object between the captured images; and
performing a shake correction process on the captured images based on the detected motion amount;
wherein:
the shake correction parameter information is selected to correspond to the observation state of the imaging section attached to the endoscope apparatus; and
the motion amount is detected using a detection method that corresponds to the selected shake correction parameter information; and
the processor performs operations further comprising:
switching a light source between a white light source that emits white light and a special light source that emits special light, the special light being light within a specific wavelength band,
detecting a light source that emits light applied to an object, and accessing a storage device that stores a plurality of pieces of shake correction parameter information that respectively correspond to a plurality of light sources, and
selecting the shake correction parameter information from the plurality of pieces of shake correction parameter information stored in the storage device to correspond to the detected light source.

6. The endoscope apparatus as defined in claim 5, wherein:
the storage device stores a plurality of pieces of shake correction parameter information that indicate a level of the shake correction process; and
the shake correction parameter information is selected to correspond to a first level when the captured images are white light images acquired by applying the white light, and to correspond to a second level lower than the first level when the captured images are special light images acquired by applying the special light.

7. The endoscope apparatus as defined in claim 5, wherein the specific wavelength band is narrower than a wavelength band of the white light.

8. The endoscope apparatus as defined in claim 7, wherein:
the white light images and the special light images are in vivo images, and
the specific wavelength band included in the in vivo images is a wavelength band of light absorbed by hemoglobin in blood.

9. The endoscope apparatus as defined in claim 8, wherein the specific wavelength band is 390 to 445 nm or 530 to 550 nm.

10. The endoscope apparatus as defined in claim 5, wherein:
- the white light images and the special light images are in vivo images, and
- the specific wavelength band included in the in vivo images is a wavelength band of fluorescence produced by a fluorescent substance.

11. The endoscope apparatus as defined in claim 10, wherein the specific wavelength band is 490 to 625 nm.

* * * * *